(12) United States Patent
Gianotti

(10) Patent No.: US 9,623,216 B2
(45) Date of Patent: Apr. 18, 2017

(54) LENGTH AND DIAMETER ADJUSTABLE BALLOON CATHETER FOR DRUG DELIVERY

(71) Applicant: ABBOTT CARDIOVASCULAR SYSTEMS INC., Santa Clara, CA (US)

(72) Inventor: Marc Gianotti, Wiesendangen (CH)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 558 days.

(21) Appl. No.: 13/797,596

(22) Filed: Mar. 12, 2013

(65) Prior Publication Data
US 2014/0276530 A1    Sep. 18, 2014

(51) Int. Cl.
*A61M 25/10*    (2013.01)
*A61M 25/00*    (2006.01)

(52) U.S. Cl.
CPC .......... *A61M 25/104* (2013.01); *A61M 25/10* (2013.01); *A61M 25/1002* (2013.01);
(Continued)

(58) Field of Classification Search
CPC .......... A61M 25/1006; A61M 25/1011; A61M 2025/1081; A61M 2025/1086;
(Continued)

(56) References Cited

U.S. PATENT DOCUMENTS

| 4,748,982 A | 6/1988 | Horzewski et al. |
| 4,782,834 A | 11/1988 | Maguire et al. |

(Continued)

FOREIGN PATENT DOCUMENTS

| EP | 0275230 | 7/1988 |
| EP | 2 450 010 | 5/2012 |

(Continued)

OTHER PUBLICATIONS

U.S. Appl. No. 13/797,766, Oct. 14, 2015 Non-Final Office Action.
(Continued)

*Primary Examiner* — Laura Bouchelle
*Assistant Examiner* — Anh Bui
(74) *Attorney, Agent, or Firm* — Baker Botts L.L.P.

(57) ABSTRACT

Adjustable balloon catheter including an inner tubular member having a proximal end portion, a distal end portion, an inflation lumen and a fluid lumen defined therein. An expandable member is coupled to the distal end portion and has an inner chamber defined therein in fluid communication with the inflation lumen, the expandable member transitionable between a deflated and inflated configuration. The expandable member further has an exterior surface, the exterior surface having at least one pore structure defined therein in fluid communication with the fluid lumen. An outer tubular member is movable relative to the inner tubular member, the outer tubular member, the outer tubular member being moveable between an extended position and a retracted position, the outer tubular member being selectively positioned between the extended position and the retracted position to define an exposed length of the working length of the expandable member.

35 Claims, 15 Drawing Sheets

(52) U.S. Cl.
CPC .... *A61M 25/1006* (2013.01); *A61M 25/1011* (2013.01); *A61M 2025/0004* (2013.01); *A61M 2025/1004* (2013.01); *A61M 2025/105* (2013.01); *A61M 2025/1068* (2013.01); *A61M 2025/1075* (2013.01); *A61M 2025/1079* (2013.01); *A61M 2025/1081* (2013.01)

(58) Field of Classification Search
CPC .... A61M 2025/105; A61M 2025/1068; A61M 2025/1075; A61M 2025/1004; A61M 2025/1079; A61M 2025/0004
See application file for complete search history.

(56) References Cited

U.S. PATENT DOCUMENTS

| | | | |
|---|---|---|---|
| 4,976,690 | A | 12/1990 | Solar et al. |
| 5,102,402 | A | 4/1992 | Dror et al. |
| 5,246,421 | A | 9/1993 | Saab |
| 5,295,959 | A * | 3/1994 | Gurbel ............... A61M 25/104 604/103 |
| 5,300,085 | A | 4/1994 | Yock et al. |
| 5,370,655 | A | 12/1994 | Burns |
| 5,423,754 | A | 6/1995 | Cornelius et al. |
| 5,454,795 | A | 10/1995 | Samson |
| 5,496,346 | A | 3/1996 | Horzewski et al. |
| 5,514,093 | A | 5/1996 | Ellis et al. |
| 5,549,551 | A * | 8/1996 | Peacock, III .......... A61F 2/958 604/103.05 |
| 5,611,775 | A * | 3/1997 | Machold ............ A61M 25/1011 604/103.01 |
| 5,626,600 | A | 5/1997 | Horzewski et al. |
| 5,649,909 | A | 7/1997 | Cornelius et al. |
| 5,676,654 | A | 10/1997 | Ellis et al. |
| 5,702,373 | A | 12/1997 | Samson |
| 5,735,816 | A | 4/1998 | Lieber et al. |
| 5,961,536 | A | 10/1999 | Mickley et al. |
| 6,129,705 | A | 10/2000 | Grantz |
| 6,174,327 | B1 | 1/2001 | Mertens et al. |
| 6,234,951 | B1 | 5/2001 | Hastings |
| 6,287,285 | B1 | 9/2001 | Michal et al. |
| 6,352,501 | B1 | 3/2002 | Urick |
| 6,406,457 | B1 | 6/2002 | Wang et al. |
| 6,495,152 | B2 | 12/2002 | Steinbuchel et al. |
| 6,500,148 | B1 | 12/2002 | Pinchuck et al. |
| 6,506,180 | B1 | 1/2003 | Lary |
| 6,541,116 | B2 | 4/2003 | Michal et al. |
| 6,579,277 | B1 | 6/2003 | Rabiner et al. |
| 6,669,980 | B2 | 12/2003 | Hansen et al. |
| 6,695,863 | B1 | 2/2004 | Ramzipoor et al. |
| 6,884,257 | B1 | 4/2005 | Cox |
| 7,241,344 | B2 | 7/2007 | Worsham et al. |
| 7,780,716 | B2 | 8/2010 | Pappas et al. |
| 7,794,489 | B2 | 9/2010 | Shumer et al. |
| 7,799,065 | B2 | 9/2010 | Pappas et al. |
| 7,828,766 | B2 | 11/2010 | Durcan et al. |
| 8,080,048 | B2 | 12/2011 | Andreas et al. |
| 8,431,145 | B2 | 4/2013 | Toner et al. |
| 2002/0009535 | A1 | 1/2002 | Michal et al. |
| 2002/0082552 | A1 * | 6/2002 | Ding ..................... A61F 2/86 604/103.02 |
| 2002/0183716 | A1 * | 12/2002 | Herweck ............... A61L 29/041 604/509 |
| 2004/0193139 | A1 | 9/2004 | Armstrong et al. |
| 2004/0234748 | A1 | 11/2004 | Stenzel |
| 2005/0182475 | A1 | 8/2005 | Jen et al. |
| 2006/0195136 | A1 | 8/2006 | Yokoyama et al. |
| 2007/0060880 | A1 | 3/2007 | Gregorich et al. |
| 2007/0088255 | A1 | 4/2007 | Toner et al. |
| 2007/0088323 | A1 | 4/2007 | Campbell et al. |
| 2007/0191864 | A1 | 8/2007 | Shumer et al. |
| 2007/0244501 | A1 | 10/2007 | Horn |
| 2008/0058722 | A1 | 3/2008 | Von Oepen et al. |
| 2008/0172037 | A1 | 7/2008 | Huang et al. |
| 2009/0105686 | A1 | 4/2009 | Snow et al. |
| 2009/0157043 | A1 * | 6/2009 | Leonard ............... A61M 31/00 604/509 |
| 2009/0254063 | A1 | 10/2009 | von Oepen et al. |
| 2010/0030183 | A1 | 2/2010 | Toner et al. |
| 2011/0028784 | A1 | 2/2011 | Patil et al. |
| 2011/0125132 | A1 | 5/2011 | Krolik |
| 2011/0143014 | A1 | 6/2011 | Stankus et al. |
| 2011/0218494 | A1 * | 9/2011 | Gerrans .......... A61B 17/320725 604/101.05 |
| 2012/0035588 | A1 | 2/2012 | Schoenle et al. |
| 2012/0116490 | A1 | 5/2012 | Wesselmann et al. |
| 2012/0232640 | A1 | 9/2012 | Horvers |
| 2012/0296313 | A1 | 11/2012 | Andreacchi et al. |
| 2012/0316638 | A1 | 12/2012 | Grad |
| 2013/0237950 | A1 | 9/2013 | Gianotti et al. |
| 2013/0253467 | A1 | 9/2013 | Gianotti et al. |

FOREIGN PATENT DOCUMENTS

| | | |
|---|---|---|
| WO | WO 81/02109 | 8/1981 |
| WO | WO 96/40349 | 12/1996 |
| WO | WO 2007/095125 | 8/2007 |
| WO | WO 2009/005933 | 1/2009 |
| WO | WO 2012/037507 | 2/2012 |
| WO | WO 2012/037510 | 3/2012 |

OTHER PUBLICATIONS

U.S. Appl. No. 13/797,766, Jul. 24, 2015 Response to Non-Final Office Action.
U.S. Appl. No. 13/797,766, Apr. 24, 2015 Non-Final Office Action.
International Search Report and Written Opinion for PCT/US2014/025366, dated Sep. 10, 2014.
U.S. Appl. No. 14/208,033, filed Mar. 13, 2014.
International Search Report and Written Opinion for PCT/US2013/068310, dated Jul. 17, 2014.
International Search Report and Written Opinion for PCT/US2013/030341, dated Dec. 3, 2013.
U.S. Appl. No. 13/793,620, filed Mar. 11, 2013.
U.S. Appl. No. 13/797,766, filed Mar. 12, 2013.
International Search Report and Written Opinion for PCT/US2011/052018, dated Nov. 15, 2011.
International Search Report and Written Opinion for PCT/US2011/052014, dated Nov. 17, 2011.
U.S. Appl. No. 13/797,766, Mar. 31, 2016 Issue Fee Payment.
U.S. Appl. No. 13/793,620, Feb. 25, 2016 Response to Non-Final Office Action.
U.S. Appl. No. 13/793,620, Nov. 25, 2015 Non-Final Office Action.
U.S. Appl. No. 13/797,766, Feb. 9, 2016 Notice of Allowance.
U.S. Appl. No. 13/797,766, Jan. 14, 2016 Response to Non-Final Office Action.
U.S. Appl. No. 13/793,620, Oct. 18, 2016 Non-Final Office Action.
U.S. Appl. No. 13/793,620, Jun. 29, 2016 Amendment and Request for Continued Examination (RCE).
U.S. Appl. No. 13/793,620, Mar. 29, 2016 Final Office Action.
U.S. Appl. No. 14/208,033, Nov. 2, 2016 Response to Restriction Requirement.
U.S. Appl. No. 14/208,033, Sep. 2, 2016 Restriction Requirement Filed.
Profile Definition, Merriam-Webster Inc., 2015.

* cited by examiner

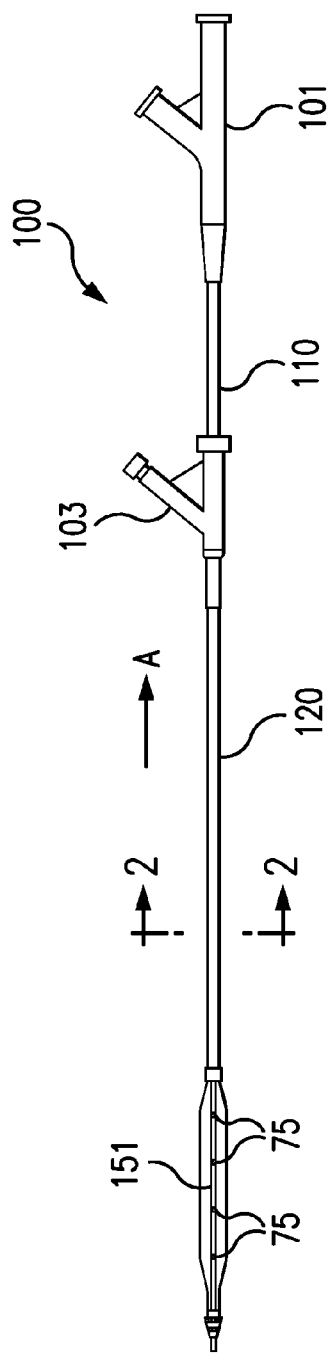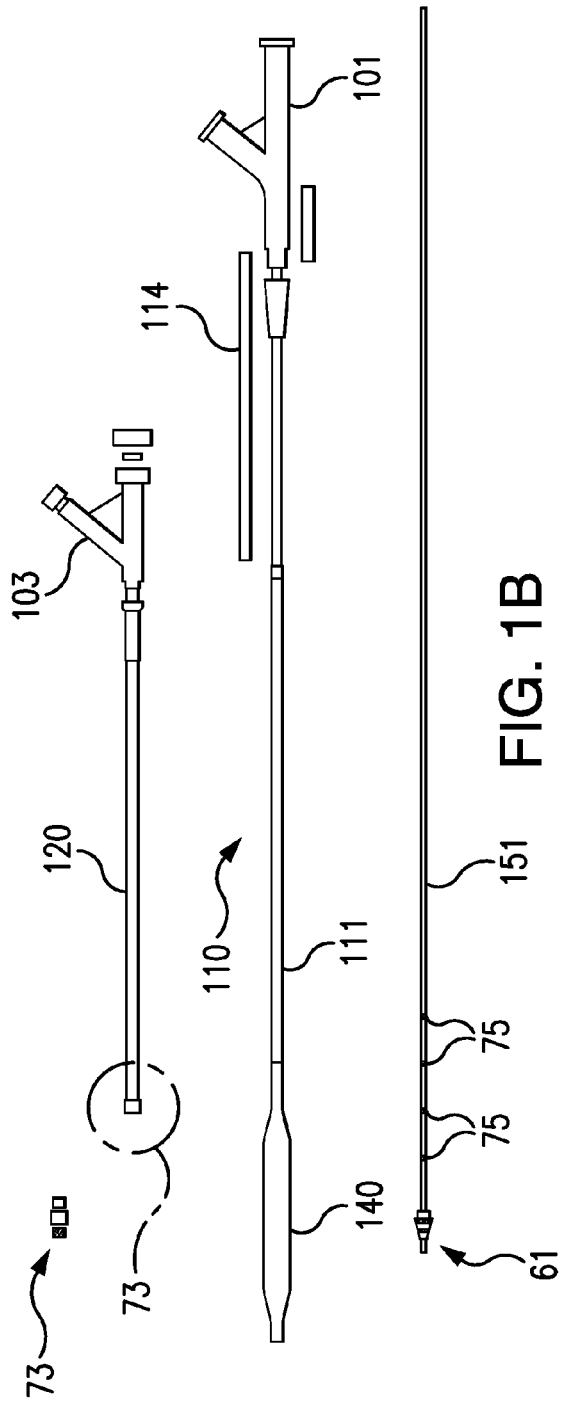
FIG. 1A
FIG. 1B

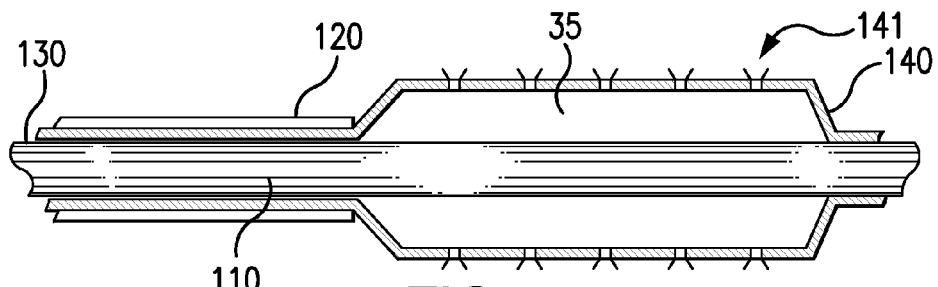
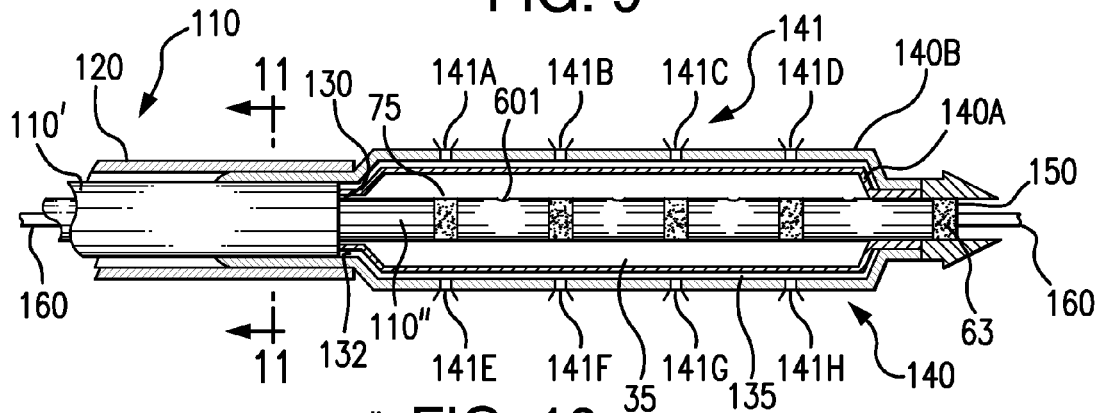
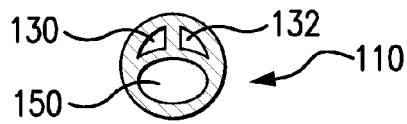
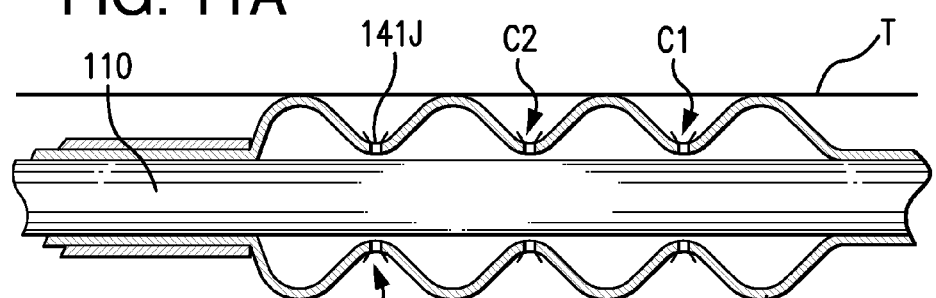
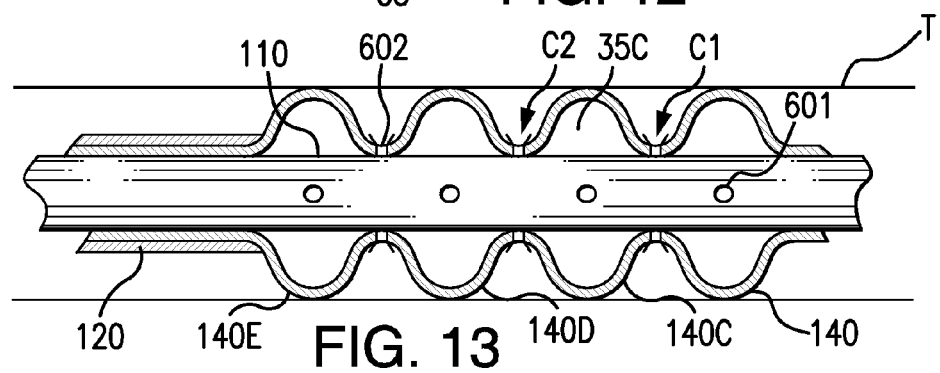

LENGTH AND DIAMETER ADJUSTABLE BALLOON CATHETER FOR DRUG DELIVERY

BACKGROUND OF THE DISCLOSED SUBJECT MATTER

Field of the Disclosed Subject Matter

The disclosed subject matter relates to adjustable balloon catheters for treating the luminal systems of a patient. Specifically, the disclosed subject matter relates to catheters having an outer tubular member movable relative to the inner tubular member to define an exposed length of an expandable member.

Description of the Related Art

A variety of catheter devices are known in the art for treating the luminal system of a patient. Of such devices, many are directed to treating vascular systems, including both the cardiovascular system and the peripheral system of a patient. For example, the treatment of the cardiovascular system can include the performance of angioplasty or delivery of balloon-expandable or self-expanding interventional devices (e.g., stents, filters, coils). The treatment of the peripheral system can include, but is not limited to, the treatment of the carotid, popliteal and renal vessels, as well as the venous systems.

One such cardiovascular system treatment includes percutaneous transluminal coronary angioplasty (PTCA); a procedure for treating heart disease. This procedure generally entails introducing a catheter assembly into the cardiovascular system of a patient via the brachial or femoral artery, and advancing the catheter assembly through the coronary vasculature until a balloon portion thereon is positioned across an occlusive lesion. Once in position across the lesion, the balloon is inflated to a predetermined size to radially compress against the atherosclerotic plaque of the lesion to remodel the vessel wall. Subsequently, the balloon is deflated to allow the catheter assembly to be withdrawn from the vasculature.

With treatment of the peripheral system, conventional catheters are configured to treat a specific type of lesion, such as short, long, diffuse, or focal lesions. As such, it is necessary to select in advance the corresponding balloon catheter to treat the lesion of interest. However, conventional catheters are not configured to treat multiple lesions at a single time.

Furthermore, the site of the occlusive lesion can often only be reached by a tortuous pathway through the vasculature of the patient. The difficulty in accessing such regions requires that a successful catheter must be sufficiently flexible longitudinally to follow the tortuous path to the desired site, and at the same time, sufficiently stiff axially to allow the distal end of the catheter to be pushed or otherwise manipulated from an external access location.

To address this problem, catheters having varied flexibility along their length have been developed. For example, each of U.S. Pat. No. 4,782,834 to Maguire and U.S. Pat. No. 5,370,655 to Burns discloses a catheter having sections along its length which are formed from materials having a different stiffness; U.S. Pat. No. 4,976,690 to Solar discloses a catheter having an intermediate waist portion which provides increased flexibility along the catheter shaft; U.S. Pat. No. 5,423,754 to Cornelius discloses a catheter having a greater flexibility at its distal portion due to both a material and dimensional transition in the shaft; and U.S. Pat. No. 5,649,909 to Cornelius discloses a catheter having a proximal portion with greater stiffness due to the application of a polymeric coating thereto.

Such conventional methods and systems generally have been considered satisfactory for their intended purpose. However, there remains a continued need in the art for an improved catheter having varied flexibility to enhance pushability, kink resistance and versatility.

In addition to PTA, PTCA, and atherectomy procedures, commonly, adjustable balloon catheters are used to the peripheral system such as in the venous system or the like. For instance, an adjustable balloon catheter is initially advanced over a guidewire to position the balloon adjacent a stenotic lesion. Once in place, the balloon is then inflated, and the restriction of the vessel is opened. Typically, balloon catheters are structured with a balloon fastened at least at one end to the exterior of a hollow catheter shaft. The hollow interior of the balloon is in a fluid flow relation with the hollow interior of the shaft. Fluid under pressure can thereby be supplied to the interior of the balloon through the shaft in order to expand the balloon against an obstruction. Unlike balloons used for cardiovascular indications, however, balloons for peripheral indications or treatments are generally much longer in length, for example, approximately 220 mm or more.

Catheter balloons typically are of a fixed length and diameter, necessitating the use of different sizes of balloons, for example, to treat vessels of varying diameter and lesions or occlusions of varying lengths.

In addition to the above-described uses of balloon catheters in PTA, PTCA, atherectomy and peripheral system procedures, other balloon catheters can be used to deliver therapeutic drugs or agents. For example, the drug can be coated on the exterior of the balloon. However, such arrangements do not allow for the selections of the desired length or dose of treatment once applied to the surface of the balloon. Furthermore, when such delivery methods are used to deliver a controlled volume of medication to a desired tissue location, the therapeutic agent can be wiped off the surface of the balloon during delivery through the tortuous lumen system or otherwise lost to systemic circulation.

In light of the foregoing, there is a need for an improved balloon catheter having enhanced pushability and crossability, adjustability of the balloon catheter in vivo, and enhanced protectability of any drugs positioned on an expandable member of the balloon catheter. Embodiments of the disclosed subject matter provide solutions for these issues.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes an adjustable balloon catheter comprising an inner tubular member having a proximal end portion, a distal end portion, and a length therebetween, the inner tubular member further having an inflation lumen and a fluid lumen defined therein. An expandable member is coupled to the distal end portion of the inner tubular member and has an inner chamber defined therein in fluid communication with the inflation lumen, the expandable member transitionable between a deflated configuration and an inflated configuration. The expandable member further has an exterior surface along a working length thereof, the exterior surface having at least one pore structure defined therein in fluid communication with the fluid lumen. An outer tubular member is movable relative to the inner tubular member, the outer tubular member including a distal end, the outer tubular member being moveable between an extended position disposed over the expandable member and a retracted position proximal to the extended position, the outer tubular member being selectively positioned between the extended position and the retracted position to define an exposed length of the working length of the expandable member.

Further in accordance with another aspect of the disclosed subject matter, an adjustable balloon catheter comprising an inner tubular member having a proximal end portion, a distal end portion, and a length therebetween, the inner tubular member further having an inflation lumen defined therein. An expandable member is coupled to the distal end portion of the inner tubular member and having an inner chamber defined therein in fluid communication with the inflation lumen, the expandable member transitionable between a deflated configuration and an inflated configuration. The expandable member further has an exterior surface along a working length thereof, the exterior surface defining at least a portion of a compartment along the working length of the expandable member when in the inflated configuration, the exterior surface further having a beneficial agent release structure associated therewith in communication with the compartment. An outer tubular member is movable relative to the inner tubular member, the outer tubular member including a distal end, the outer tubular member being moveable between an extended position disposed over the expandable member and a retracted position proximal to the extended position, the outer tubular member being selectively positioned between the extended position and the retracted position to define an exposed length of the working length of the expandable member.

Further in accordance with another aspect of the disclosed subject matter, a method of delivering a beneficial agent using one of the adjustable balloon catheters discussed herein. For example, the method can, comprise providing an adjustable balloon catheter including an inner tubular member having a proximal end portion, a distal end portion, and a length therebetween. The inner tubular member can further have an inflation lumen and a fluid lumen defined therein. An expandable member is coupled to the distal end portion of the inner tubular member and has an inner chamber defined therein in fluid communication with the inflation lumen, the expandable member transitionable between a deflated configuration and an inflated configuration. The expandable member further has an exterior surface along a working length thereof, the exterior surface having at least one pore structure defined therein in fluid communication with the fluid lumen. An outer tubular member is movable relative to the inner tubular member, the outer tubular member including a distal end, the outer tubular member being moveable between an extended position disposed over the expandable member and a retracted position proximal to the extended position. The outer tubular member is selectively positioned between the extended position and the retracted position to define an exposed length of the working length of the expandable member. The method further includes retracting the outer tubular member in a proximal direction to define the exposed length of the working length of the expandable member and inflating the exposed length of the expandable member to the inflated configuration. The method further includes releasing beneficial agent from the at least one pore structure and deflating the expandable member to the deflated configuration.

Further in accordance with another aspect of the disclosed subject matter, a method of delivering a beneficial agent using one of the adjustable balloon catheters discussed herein. For example, the method can, comprise providing an adjustable balloon catheter including an inner tubular member having a proximal end portion, a distal end portion, and a length therebetween, the inner tubular member further having an inflation lumen and a fluid lumen defined therein. An expandable member is coupled to the distal end portion of the inner tubular member and having an inner chamber defined therein in fluid communication with the inflation lumen, the expandable member transitionable between a deflated configuration and an inflated configuration. The expandable member further has an exterior surface along a working length thereof, the exterior surface defining at least one a portion of a compartment along the working length of the expandable member when in the inflated configuration, the exterior surface further having a beneficial agent release structure associated therewith in communication with the at least one compartment. An outer tubular member is movable relative to the inner tubular member, the outer tubular member including a distal end, the outer tubular member being moveable between an extended position disposed over the expandable member and a retracted position proximal to the extended position, the outer tubular member being selectively positioned between the extended position and the retracted position to define an exposed length of the working length of the expandable member. The method further includes retracting the outer tubular member in a proximal direction to define the exposed length of the working length of the expandable member and inflating the exposed length of the expandable member to the inflated configuration with the compartment along the exposed length. The beneficial agent is released from the beneficial agent release structure into the compartment and the expandable member is deflated to the deflated configuration.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

FIG. 1A is a side view of a representative balloon catheter in the inflated condition in accordance with the disclosed subject matter.

FIG. 1B is an exploded side view of the representative balloon catheter of FIG. 1A in accordance with the disclosed subject matter.

FIG. 9 is a partial cross-sectional side view of a distal end of an adjustable balloon catheter for delivery of a beneficial agent, according to the disclosed subject matter.

FIG. 10 is a partial cross-sectional side view of a distal end of an adjustable balloon catheter for delivery of a beneficial agent, according to another embodiment of the disclosed subject matter.

FIG. 11A is a cross sectional view of the inner tubular member of FIG. 10 taken along line 11-11 wherein the inner tubular member has a coaxial configuration, according to an embodiment of the disclosed subject matter.

FIG. 11B depicts an alternate embodiment of the cross section of the inner tubular member taken along line 11-11, where in the inner tubular member has a multi-lumen arrangement, according to an embodiment of the disclosed subject matter.

FIG. 12 is a partial cross-sectional side view of a distal end of an adjustable balloon catheter for delivery of a beneficial agent, according to another embodiment of the disclosed subject matter.

FIG. 13 is a partial cross-sectional view of a distal end of the adjustable balloon catheter generally having a plurality of expandable members, according to another embodiment of the disclosed subject matter.

DETAILED DESCRIPTION

Figure 2:
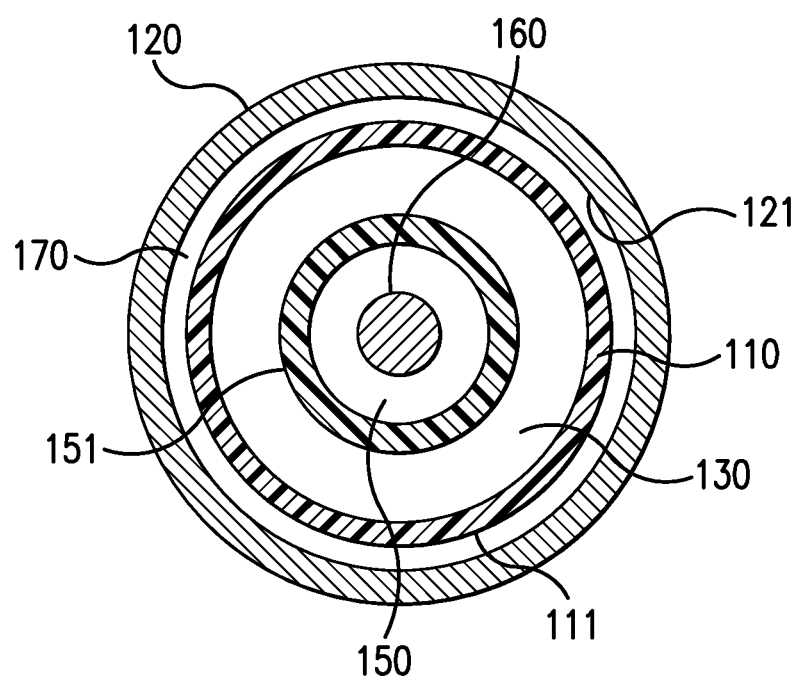
FIG. 2 is a cross sectional view of the catheter of FIG. 1A taken along line 2-2 wherein the inner tubular member has a coaxial configuration according to an embodiment of the disclosed subject matter.

As disclosed herein, the devices presented herein can be used for treating the luminal system of a patient. The disclosed subject matter is particularly suited for the delivery of a beneficial agent for treatment of the cardiovascular system and/or the peripheral system of a patient. The treatment of the cardiovascular system includes the performance of angioplasty or delivery of balloon-expandable or self-expanding interventional devices (e.g., stents, filters, coils). The treatment of the peripheral system includes, but is not limited to, treatment of the carotid, popliteal and renal vessels. Accordingly, the presently disclosed subject matter is also suitable for a variety of particular endovascular vessels.

In accordance with one aspect of the disclosed subject matter, an adjustable balloon catheter is provided. The adjustable balloon catheter comprises an inner tubular member having a proximal end portion, a distal end portion, and a length therebetween, the inner tubular member further having an inflation lumen and a fluid lumen defined therein. An expandable member is coupled to the distal end portion of the inner tubular member and has an inner chamber defined therein in fluid communication with the inflation lumen, the expandable member transitionable between a deflated configuration and an inflated configuration. The expandable member further has an exterior surface along a working length thereof, the exterior surface having at least one pore structure defined therein in fluid communication with the fluid lumen. An outer tubular member is movable relative to the inner tubular member, the outer tubular member including a distal end, the outer tubular member being moveable between an extended position disposed over the expandable member and a retracted position proximal to the extended position, the outer tubular member being selectively positioned between the extended position and the retracted position to define an exposed length of the working length of the expandable member.

Further in accordance with another aspect of the disclosed subject matter, an adjustable balloon catheter comprising an inner tubular member having a proximal end portion, a distal end portion, and a length therebetween, the inner tubular member further having an inflation lumen defined therein. An expandable member is coupled to the distal end portion of the inner tubular member and having an inner chamber defined therein in fluid communication with the inflation lumen, the expandable member transitionable between a deflated configuration and an inflated configuration. The expandable member further has an exterior surface along a working length thereof, the exterior surface defining at least a portion of a compartment along the working length of the expandable member when in the inflated configuration, the exterior surface further having a beneficial agent release structure associated therewith in communication with the compartment. An outer tubular member is movable relative to the inner tubular member, the outer tubular member including a distal end, the outer tubular member being moveable between an extended position disposed over the expandable member and a retracted position proximal to the extended position, the outer tubular member being selectively positioned between the extended position and the retracted position to define an exposed length of the working length of the expandable member.

Further in accordance with another aspect of the disclosed subject matter, a method of delivering a beneficial agent using one of the adjustable balloon catheters discussed herein. For example, the method can comprise providing an adjustable balloon catheter including an inner tubular member having a proximal end portion, a distal end portion, and a length therebetween. The inner tubular member can further have an inflation lumen and a fluid lumen defined therein. An expandable member is coupled to the distal end portion of the inner tubular member and has an inner chamber defined therein in fluid communication with the inflation lumen, the expandable member transitionable between a deflated configuration and an inflated configuration. The expandable member further has an exterior surface along a working length thereof, the exterior surface having at least one pore structure defined therein in fluid communication with the fluid lumen. An outer tubular member is movable relative to the inner tubular member, the outer tubular member including a distal end, the outer tubular member being moveable between an extended position disposed over the expandable member and a retracted position proximal to the extended position. The outer tubular member is selectively positioned between the extended position and the retracted position to define an exposed length of the working length of the expandable member. The method further includes retracting the outer tubular member in a proximal direction to define the exposed length of the working length of the expandable member and inflating the exposed length of the expandable member to the inflated configuration. The method further includes releasing beneficial agent from the at least one pore structure and deflating the expandable member to the deflated configuration.

Further in accordance with another aspect of the disclosed subject matter, a method of delivering a beneficial agent using one of the adjustable balloon catheters discussed herein. For example, the method can comprise providing an adjustable balloon catheter including an inner tubular member having a proximal end portion, a distal end portion, and a length therebetween, the inner tubular member further having an inflation lumen and a fluid lumen defined therein. An expandable member is coupled to the distal end portion of the inner tubular member and having an inner chamber defined therein in fluid communication with the inflation lumen, the expandable member transitionable between a deflated configuration and an inflated configuration. The expandable member further has an exterior surface along a working length thereof, the exterior surface defining at least a portion of a compartment along the working length of the expandable member when in the inflated configuration, the exterior surface further having a beneficial agent release structure associated therewith in communication with the at least one compartment. An outer tubular member is movable relative to the inner tubular member, the outer tubular member including a distal end, the outer tubular member being moveable between an extended position disposed over the expandable member and a retracted position proximal to the extended position, the outer tubular member being selectively positioned between the extended position and the retracted position to define an exposed length of the working length of the expandable member. The method further includes retracting the outer tubular member in a proximal direction to define the exposed length of the working length of the expandable member and inflating the exposed length of the expandable member to the inflated configuration with the compartment along the exposed length. The beneficial agent is released from the beneficial agent release structure into the compartment and the expandable member is deflated to the deflated configuration.

Reference will now be made in detail to embodiments of the disclosed subject matter, an example of which is illustrated in the accompanying drawings. The disclosed subject matter will be described in conjunction with the detailed description of the system.

For purpose of explanation and illustration, and not limitation, an embodiment of an adjustable balloon catheter, at least a portion of which is delivered within a vasculature, is shown schematically in FIG. 1A. FIG. 1B is an exploded view of FIG. 1A. Particularly and as illustrated, the adjustable balloon catheter 100 includes an inner tubular member (or catheter shaft) 110 having a proximal end portion, a distal end portion, and a length therebetween. The inner tubular member 110 can include a variety of suitable configurations. For example, but not limitation, in one embodiment the inner tubular member can comprise an over-the-wire (OTW) configuration. In this embodiment, the inner tubular member includes a guidewire lumen 150 extending generally across the entire length of the inner tubular member. A guidewire 160 can be introduced into the guidewire lumen 150, in a conventional manner as known.

Alternatively, the catheter can be configured with a rapid exchange configuration (RX). In this embodiment, a guidewire lumen 150 extends to a proximal guidewire port spaced distally from a proximal end portion of the inner tubular member. In either the OTW or the RX configuration, the inner tubular member can be provided with a co-axial arrangement or a multi-lumen arrangement. Further, the inner tubular member can be a single tube or an assembly of compartments coupled together along its length. For purpose of example, and not limitation, the inner tubular member of the catheter embodied herein for peripheral vascular use includes a L12 shaft with an outer diameter of approximately 1.08 mm, and a length of approximately 120 cm. Those skilled in the art will recognize that other configurations and known materials of construction can be used without departing from the scope of the disclosed subject matter.

For example, and as shown in FIG. 2, for the purpose of illustration and not limitation, a representative cross-sectional view of a co-axial arrangement is provided. The cross-sectional view is taken along lines 2-2 of FIG. 1A. In this manner, the inner tubular member can further include a guidewire tube 151 defining the guidewire lumen 150 therein, and an inflation lumen 130 defined annularly between the inner tubular member 110 and the guidewire tube 151. Further, the guidewire lumen can be formed by a thin membrane of suitable strength to prevent the guidewire from penetrating therethrough and minimize increases in cross-sectional profile of the inner tubular member. Alternatively, the guidewire tube 151 can be a multilayer construction, such as, but not limited to, a layer of Nylon-L25, a bonding layer such as Prim, and a layer of high-density polyethylene (HDPE).

Figure 3:
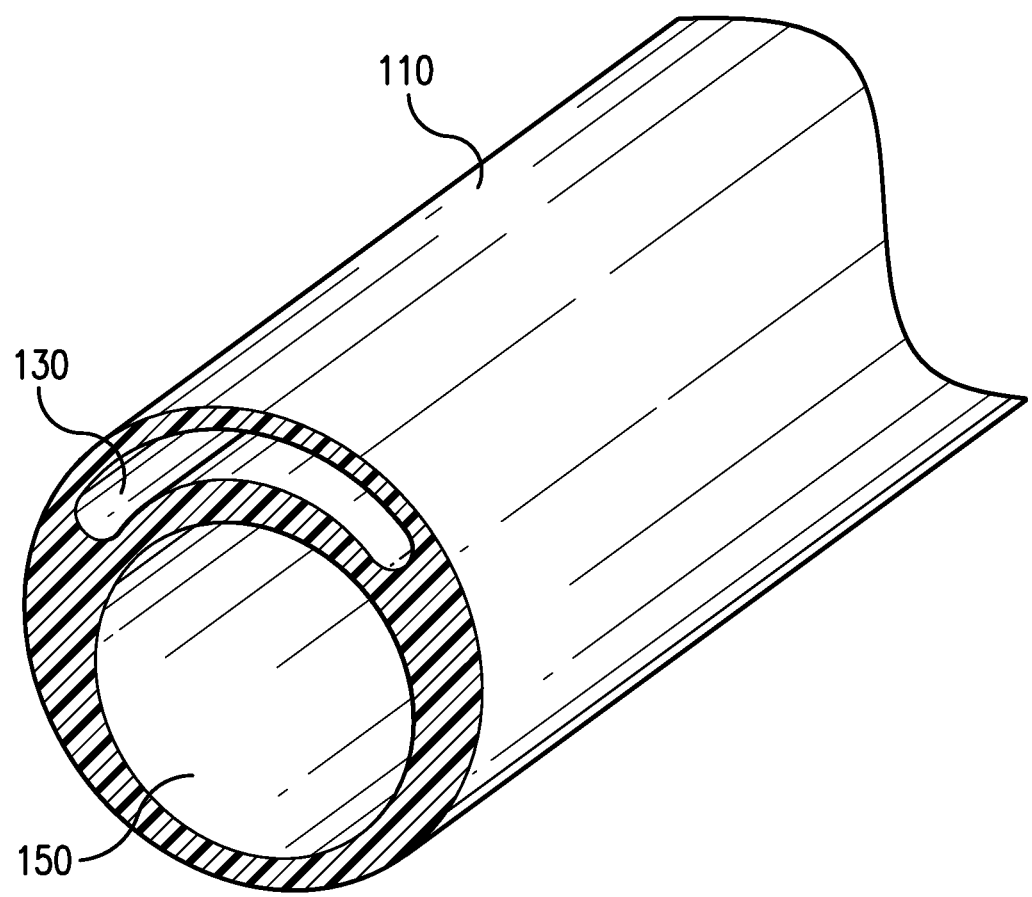
FIG. 3 is a cross-sectional view of an inner tubular member having a multilumen configuration, according to another embodiment of the disclosed subject matter.

In accordance with another embodiment, as depicted in FIG. 3, the inner tubular member can be a multi-lumen arrangement. For example, but not limitation, the inner tubular member 110 can be a monolithic member with the multi-lumen arrangement. In such embodiment, the inner tubular member 110 defines an inflation lumen 130 and a guidewire lumen 150, therein. The guidewire lumen 150 permits the catheter 100 to be delivered over a guidewire 151.

In either embodiment, the inner tubular member 110 comprises an exterior surface 111 and defines the inflation lumen 130 therein. The inflation lumen is in fluid communication with the inner chamber of the expandable member 140, as described further below. The inflation lumen 130 defines a pathway for fluid to travel along the inner tubular member 110, whether fluid can be introduced into the inflation lumen 130 at a proximal end of the catheter 100 via a luer adaptor or the like. The inflation lumen 130 can supply an inflation medium under positive pressure and can withdraw the inflation medium, e.g., by negative pressure, from the expandable member. The expandable member can thus be inflated and deflated, as further discussed below.

In an alternate embodiment, the inflation lumen and the guidewire lumen are combined and comprise a single shared lumen. For such co-axial arrangements, fluid can thus flow within the shared lumen with a guidewire 151 positioned therein. In such configuration, the inner tubular member 110 can comprise proximal and distal guidewire seals to sealingly engage the guidewire 151 disposed within the inflation lumen. The shared lumen can further have a stop, alone or in addition to the seals, at the distal end to allow the guidewire to proceed past the distal end of the catheter and to prevent the fluid from escaping the shared lumen. The seal or stop provides a recess to allow the guidewire to continue in the guidewire lumen. Such coaxial configurations allow for reduced diameter of the inner tubular member, and thus reduced profile.

As further depicted in FIG. 1A, an adapter or manifold 101 can be provided at the proximal end of the catheter for access to the inflation lumen and is configured for connecting to a fluid source (not shown). The manifold can have a Y shape with a luer connector at the proximal end of one branch to receive the fluid source, and a separate hemostatic valve on another branch to receive a guidewire. A conventional device, such as but not limited to an indeflator or a syringe, can be connected to the luer connector to introduce the fluid to the inflation lumen. A locking mechanism can further be provided to lock the operating position of the indeflator or syringe.

The indeflator or other fluid source can be configured to control the inflation and deflation of the expandable member. A pressure gauge can be provided with the indeflator to monitor and/or maintain the pressure system of the catheter. The indeflator likewise can allow for the rapid release of pressure. The indeflator can have a locking mechanism to maintain negative pressure in the catheter, which can decrease the profile of the catheter. The catheter is sized and configured for delivery within a body lumen, such as a vasculature, and particularly through a tortuous anatomy.

Figure 4:
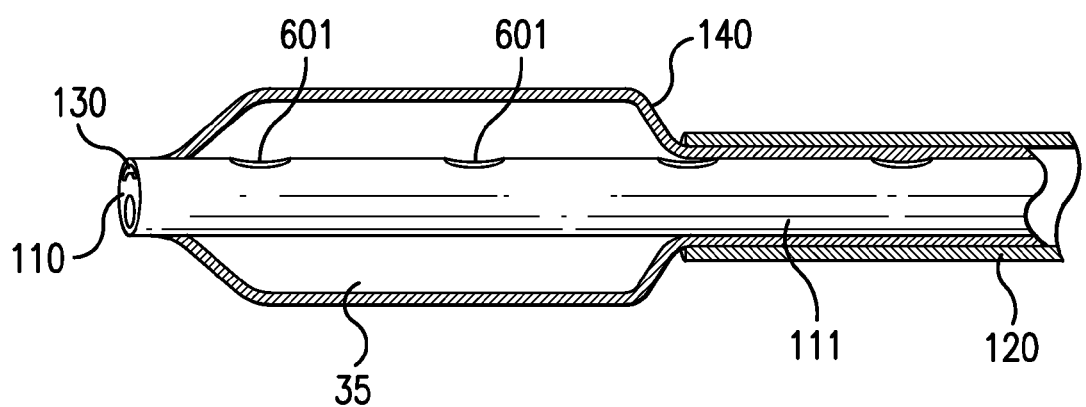
FIG. 4 is a schematic view of a catheter having a plurality of inflation ports, according to the disclosed subject matter.

As previously noted, an expandable member is coupled to the distal end portion of the inner tubular member as depicted in FIG. 1A. The expandable member 140, or balloon as depicted herein, has an exterior surface and an interior surface. The interior surface of the expandable member defines an inner chamber in fluid communication with the inflation lumen 130 of the inner tubular member. In accordance with one aspect, the inner tubular member can extend at least partially through the expandable member. For purpose of illustration and not limitation, FIG. 4 shows the inner tubular member extending the entire length of the expandable member. As embodied herein, a plurality of inflation ports 601 can be defined in the inner tubular member along the working length of the expandable member to ensure fluid communication with the inner chamber 35. The plurality of inflation ports provides enhanced inflation and deflation of the expandable member through compressed areas.

The expandable member 140 is transitionable between a deflated configuration and an inflated configuration. The outer tubular member 120, as described further below, is retracted in a proximal direction to define an exposed length of the expandable member. The expandable member has an overall length with a working length extending at least a portion of the overall length. The expandable member defines a longitudinal axis and can have a non-cylindrical shape along at least a portion of the working length thereof when in the inflated configuration. As embodied herein, for illustration and not limitation, at least a portion of the exterior surface of the expandable member along the working length is configured to engage a body lumen of a patient when the expandable member is in the inflated configuration.

In accordance with one aspect of the disclosed subject matter, a variety of different shapes can be used for the expandable member, wherein the shape of the expandable member can depend upon the desired application as will be described below.

As previously disclosed, the catheter further includes an outer tubular member or sheath. For example, and as embodied for illustration and not limitation, FIGS. 1A, 1B, and FIG. 2 illustrate the outer tubular member 120 has a proximal end, a distal end, a length, and an interior surface 121. The inner tubular member 110 is positioned within the outer tubular member 120 at the distal end of the catheter 100, such that the interior surface 121 of the outer tubular member 120 is directed toward the exterior surface 111 of the inner tubular member 110. The outer tubular member 120 is movable relative to the inner tubular member 110 along a length of the inner tubular member 110. For example, the outer tubular member 120 can be retracted in a direction A toward the proximal end of the catheter or extended distally. The outer tubular member 120 can be disposed at a distal end portion of the catheter or can extend the entire length of the catheter. The outer tubular member has a length at least equal to the length of the expandable member 140.

The outer tubular member 120 is movable relative the inner tubular member 110 between an extended position disposed over the expandable member 140 and a retracted position proximal to the extended position. The working length of the expandable member represents the maximum length that can be exposed outside the outer tubular member. The outer tubular member is selectively positioned between the extended position and the retracted position to define an exposed length of the working length of the expandable member, as further discussed herein. Additionally, the outer tubular member is selectively positioned to selectively adjust the stiffness profile and/or the flexibility profile along the length of the catheter as further described herein.

Figure 5A:
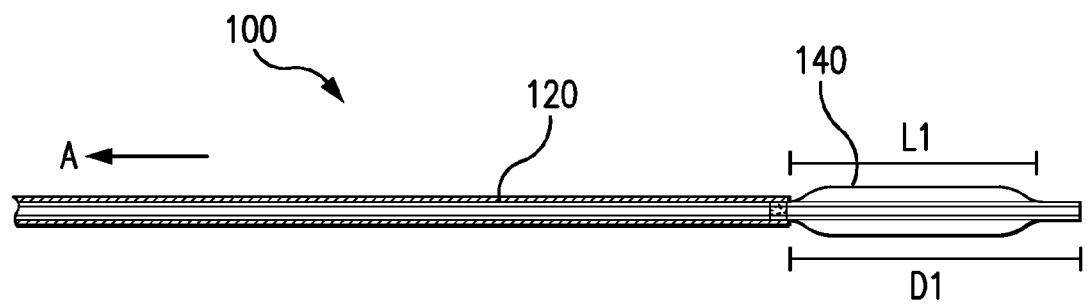
FIGS. 5A-5C are images of catheters in accordance with the disclosed subject matter with the retractable outer tubular member selectively positioned to expose various lengths of the expandable member, in accordance with an embodiment of the disclosed subject matter.
Figure 5B:
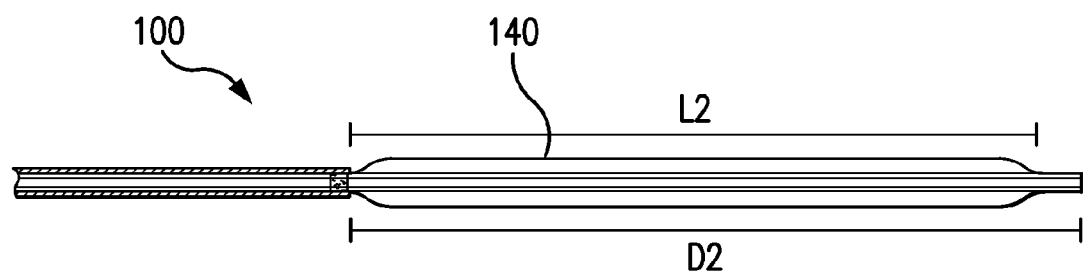
Figure 5C:
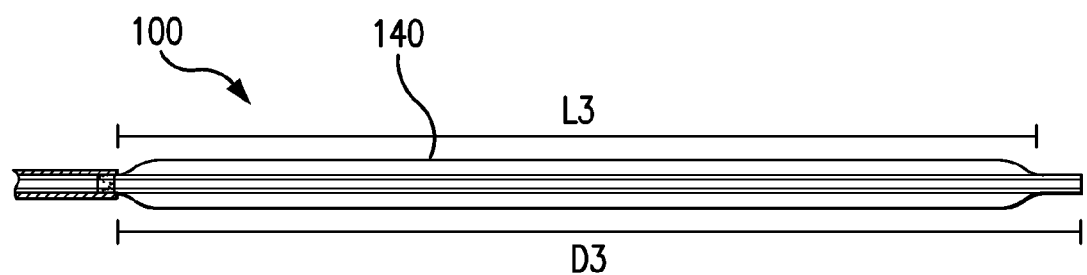

For purpose of explanation and illustration, and not limitation, FIGS. 5A-5C depict schematics of a representative catheter in accordance with the disclosed subject matter. The adjustable outer tubular member 120 is selectively positioned to expose various lengths of the expandable member. FIG. 5A depicts the adjustable outer tubular member 120 retracted a first distance D1 in the proximal direction A to expose a first exposed length L1 of the working length of the expandable member. FIG. 5B depicts the adjustable outer tubular member 120 retracted a second distance D2 to expose a second exposed length L1 of the working length of the expandable member. FIG. 5C depicts the adjustable outer tubular member 120 retracted a third distance D3 to expose a third exposed length L3 of the working length of the expandable member. The further the outer tubular member is retracted, the greater portion of the length of the balloon can be exposed.

A variety of actuators can be used to move the outer tubular member between the retracted position and the extended position. For example, the proximal end of the outer tubular member can be moved or otherwise actuated by a push-pull handle assembly. The outer tubular member can also be extended and retracted through the use of actuators as disclosed in U.S. Pat. Nos. 7,780,716 and 7,799,065, and U.S. Patent Application Publications 2005/0182475 and 2007/0191864, the contents of which are incorporated herein in their entirety.

The outer tubular member can be provided with a generally constant cross-section or diameter. Alternatively, the outer tubular member can define a first external diameter at its proximal end, and a second, different external diameter at its distal end. The first diameter can be smaller than the second diameter, or vice versa. For example, and in accordance with an embodiment of the disclosed subject matter, the outer tubular member can have a first diameter of about 4 French and a second diameter of about 5 French, although these dimensions can vary depending on the desired application.

In accordance with this aspect of the disclosed subject matter, a step can be provided to allow for the change in diameter between the proximal end and distal end of the outer tubular member. The step allows for the change in diameter to occur over a longer or shorter distance along the outer tubular member, depending on the application. Alternatively, a more gradual taper can be provided if desired.

The outer tubular member 120 protects the expandable member 140, and any coating or therapeutic agent on the expandable member as discussed further below, during delivery of the expandable member through a body lumen of a patient to the target site. In one aspect of the disclosed subject matter, the outer tubular member can prevent the release of drug from the surface of the expandable member prior to deployment at the desired site such that drug loss is minimized. The outer tubular member can be utilized to protect the coating of therapeutic agent from releasing from the expandable member during the movement of the adjustable balloon catheter through the body lumen. Furthermore, the outer tubular member can also protect the coating during shipping and storage before use.

In another aspect of the disclosed subject matter, the inner surface of the outer tubular member can be further formed having a non-uniform surface, such as a repeating pattern formed therein, the pattern forming a sinusoidal pattern about the circumference of the tubular member. By forming the surface in the manner described, frictional forces between the inner surface of the outer tubular member and the outer surface of the expandable member can be reduced by forming points of contact between the two surfaces instead of a continuous surface contact between the two surfaces. The multiple contact points reduce friction between the outer tubular member and the expandable member thereby requiring less force to retract the outer tubular member during use. The outer tubular member can be fabricated as a unitary member or fabricated of more than one element.

The outer tubular member can be constructed of a single layer of suitable material. For example, a suitable material can include, but is not limited to, polymer materials such as nylon, urethane, polyurethane, PEEK, PTFE, PVDF, Kynar, PE, HDPE, a trilayer material including L25, Plexar, or polyethylene of various suitable densities. The thickness of the single layer can vary in thickness along the length of the adjustable length catheter. Alternatively, the thickness of the single layer can remain substantially constant.

In accordance with another aspect of the disclosed subject matter, the outer tubular member can comprise a multilayer member and include, for example, an outer layer and an inner layer. The inner layer can be attached to or formed with the outer layer. For example, the multiple layers can be formed in a number of suitable manners including, but not limited to, separately and adhered or bonded together or co-extruded as a single member. The inner layer or liner can include a lubricious material to facilitate the sliding of the outer tubular member in a proximal direction when the outer tubular member is retracted. For example, different types of polymers such as PTFE or high-density polyethylene (HDPE) can be used for the inner layer. Additionally, other suitable lubricious polymers can be used. If desired, the inner layer of the outer tubular member can be formed with a varied wall thickness. For example, the wall thickness can be greater at the distal end than at the proximal end. The outer layer, alone or in combination with the inner layer, can provide sufficient strength to capture a medical device therein, as well as allow movement between extended position and the retracted position. Furthermore, the outer tubular member has sufficient axial strength or stiffness to enhance pushability of the catheter as desired and described further below.

In further accordance with the disclosed subject matter, the outer tubular member can include a reinforcing layer, such as braided material, disposed between the outer layer and the inner layer. For example, the reinforcing layer can be provided in the form of braided stainless steel filaments having rectangular or otherwise flattened cross-sections. Other woven or braided material likewise can be used, such as carbon fibers encased in a polymeric matrix. Likewise, reinforcing fibers can additionally or alternatively be incorporated between or into the inner layer and/or outer layer during the manufacturing process. The reinforcing layer need not be present through the entire length of the outer tubular member. Indeed, and in accordance with another aspect of the disclosed subject matter, the reinforcing layer can be provided or varied along selected portions of the outer tubular member or the inner tubular member to alter the flexibility and/or stiffness profiles therefrom. For example, the reinforcing layer can provided along the proximal portion the outer tubular member only. In one embodiment for purposes of illustration and not limitation, the outer tubular member can include an inner layer of PTFE with an inner diameter of 1.14 mm, a braided reinforcing layer of 0.0254 mm×0.0762 mm of 304V stainless steel wire at 25 PIC, and an outer layer of nylon with an inner diameter of 1.265 mm.

In accordance with an embodiment of the disclosed subject matter, the outer tubular member can have a wall thickness of about 6.0 mil, wherein inner layer and reinforcing layer have a thickness of about 2.0 mil, and outer layer has a thickness of about 4.0 mil. Wherein the dimensions above are provided as examples and should not be considered limiting in any manner.

When the outer tubular member is provided with an inner layer, outer layer and a reinforcing layer the outer tubular member can be formed in the following manner. First, the inner layer is formed through a tubular extrusion process, and disposed about a forming mandrel (not shown). The forming mandrel can have a shape that corresponds to the desired shape of the inside of the outer tubular member. The reinforcing layer can be provided in the form of a stainless steel braid material and is positioned over a predetermined length of inner layer, e.g. a distal portion of the inner layer can remain uncovered by the reinforcing material. The outer layer is then extruded over the reinforcing layer. The outer layer can be provided in the form of two separate tubular members that are overlapped slightly at their ends over reinforcing layer. Each portion of outer layer can be a different material selected to provide a different durometer as desired. The two portions of outer layer can overlap by an amount, such as, but not limited to, about 2.0-2.5 MM. Next, a sleeve of heat shrinkable material is positioned over the entire outer tubular member assembly. When heat is applied to the assembly, the heat shrinkable tubing shrinks and causes inner layer to fuse with outer layer, trapping reinforcing layer therebetween. The heating process also causes inner layer to conform to the shape of the forming mandrel. Thus, if it is desired to have an outer tubular member with a varied and/or stepped diameter as described above, the mandrel can be formed accordingly. After the assembly cools, the heat shrinkable tubing is cut away, leaving behind the outer tubular member 120.

The inner and outer tubular members of the adjustable balloon catheter each can be single piece construction, or an assembly of compartments, and can be made of any suitable material. For example, suitable materials include, but are not limited to polymer materials such as nylon, urethane, polyurethane, PEEK, PTFE, PVDF, Kynar, PE, HDPE, a trilayer material including L25, Plexar, or polyethylene of various suitable densities. As a further exemplary alternative, the outer tubular members can be constructed of a composite comprising a fabrication of several different materials, such as a co-extrusion of different polymers, or a fiber-reinforced composite material such as fiber reinforced resin materials or braided materials. For example and not limitation, exemplary embodiments can include a braided tube with a PTFE liner, a Polymide middle layer with braiding and a Pebax 72D outer layer, as previously described. Furthermore, a portion of the inner and/or outer tubular members can be constructed of an alloy or metallic material, such as stainless steel hypodermic tubing which is available from Micro-Group® Inc., Medway, Md. among other vendors. Other materials for the outer tubular member include PEEK; a trilayer material of L25, Plexar, HDPE; or a braided tube with a PTFE liner, a Polyimide middle layer with braiding and a Pebax 72D outer layer.

It is further contemplated that the inner and outer tubular members can be constructed of other biocompatible material. As such, the inner and outer tubular members of the adjustable balloon catheter can be constructed from the above-identified polymers, combinations or blends of these polymers, whether alone or in combination with other materials, or other bioabsorbable materials.

The inner and outer tubular members can be manufactured using a variety of known techniques such as, but not limited to, those techniques previously discussed and extrusion, injection molding, air-blowing, stretching, deep drawing, polymerization, cross-linking, dipping from solution, powder depositioning, sintering, electro-spinning, melt spinning, deformation under temperature, stretch blowing, chemical grafting any combination of the above with reinforcement element like metal braids, coils, glass fibers, carbon fibers and other kind of organic or inorganic fibers, liquid crystals, as well as classical machining technologies like milling, drilling, grinding, etc. In the event that metallic elements such as hypotubes, are to be incorporated, various metallic manufacturing techniques can be used, such as but not limited to, machining, tube drawing processes, drilling, milling EDM, other deformation methods, plating sputtering, electrografting, sintering, and depositioning e-polishing, among others. Additionally, the inner and/or outer tubular members can be constructed from polypropylene or urethane by an extrusion process using an extruder such as that available any of a number of known suppliers, such as Medical Extrusion Technologies, Inc. Murrieta, Calif. U.S. Biosynthetic polymer materials can be constructed in a bioreactor according to the process disclosed in U.S. Pat. No. 6,495,152, the entirety of which is hereby incorporated by reference. The materials can be post processed in a number of ways including, for example and not by way of limitation, extrusion, molding, such as by injection or dipping, textile processing such as weaving or braiding, and forming. Forming processes that can be suitable are rolling and welding sheets of material or vacuum forming into tubular shapes, to name only a few examples.

The inner and outer tubular members can be further coated with any of a variety of materials and techniques to enhance performance if desired, including a number suitable coatings and coating techniques subject to patent matters owned by Abbott Laboratories such as U.S. Pat. No. 6,541,116, U.S. Pat. No. 6,287,285, and U.S. Patent Publication No. 2002/0009535, the entireties of which are hereby incorporated by reference. For example, possible coating materials include lubricious materials such as Teflon® available from DuPont De Nemours, Wilmington, Del., U.S., and hydrophobic materials such as silicone lubricant dispersion PN 4097, available from Applied Silicone Corp., Ventura, Calif., U.S., or hydrophilic materials such as hydrogel available from Hydromer, Branchburg, N.J., U.S., or lubricious coatings such as those available from Hydro-Silk of Merritt Island, Fla., U.S. The inner and outer tubular members can have any suitable cross-sectional shape, including elliptical, polygon, or prismatic, although a circular cross-section is common. The inner and outer tubular members can also have any suitable size and diameter depending upon the desired application. Furthermore, in the case of a balloon catheter with a "rapid exchange" (RX) guidewire design, the adjustable balloon catheter can have an overall length between about 110 centimeters and 400 centimeters. In the case of a balloon catheter with an "over the wire" (OTW) guidewire design, the adjustable balloon catheter can have an overall length between about 110 centimeters and 400 centimeters. In one embodiment, the adjustable balloon catheter in accordance with the disclosed subject matter is a compatible 4 French introducer sheath BTK balloon device.

Figure 6:
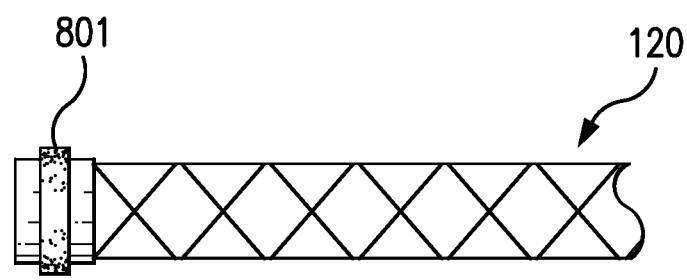
FIG. 6 is an embodiment of the outer tubular member with a braided polymer shaft, in accordance with an embodiment of the disclosed subject matter.

In accordance with another aspect of the disclosed subject matter referring to FIG. 6, for purpose of illustration and not limitation, an alternative embodiment of an outer tubular member 120 is shown. At least a portion of the outer tubular member, e.g. the distal end portion, as shown, is formed of a braided polymer sleeve with a marker 801 at its distal end. The braided polymer sleeve increases flexibility and softness of the outer tubular member. Additionally, to improve flexibility, the spiral plastics can be used in the construction of the outer tubular member. The marker can be a radiopaque metallic ring or other member suitable for the intended use. Alternatively, the marker can be constructed using tungsten loaded polymer plastics for increased softness. Other suitable known markers can be used, as further discussed herein.

In a further embodiment of the disclosed subject matter, a flushing lumen 170 is defined between the inner tubular member and the outer tubular member, as depicted in FIG.

Figure 7:
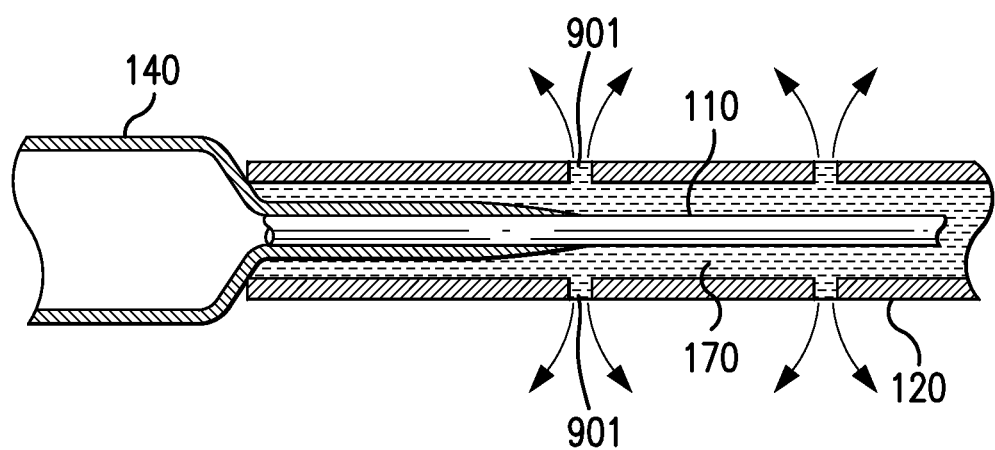
FIG. 7 is a schematic view of the outer tubular member having flushing ports, in accordance with an embodiment of the disclosed subject matter.

7. In accordance with another aspect, the outer tubular member includes at least one flushing port 901 defined therethrough in fluid communication with the flushing lumen, as depicted in FIG. 7. A fluid, such as but not limited to, a contrast media or therapeutic agent, can be introduced into the flushing lumen by an adapter in communication therewith. The contrast media or agent can exit the flushing lumen 170 via the at least one flushing port 901.

In accordance with another aspect of the disclosed subject matter, the catheter has a stiffness profile and a flexibility profile wherein at least one of the stiffness and the flexibility is selectively adjustable by the selected position of the outer tubular member relative the inner tubular member, as discussed in greater detail in PCT Application No. PCT/US2011/052014, which is incorporated in its entirety herein.

With reference again to the expandable member, it is understood that a variety of suitable shapes and materials can be employed, as discussed in detail in U.S. Publication No. 2009/0105686, entitled "Adjustable-Length Drug Delivery Balloon" the contents of which are incorporated by reference herein in its entirety.

Figure 7A:
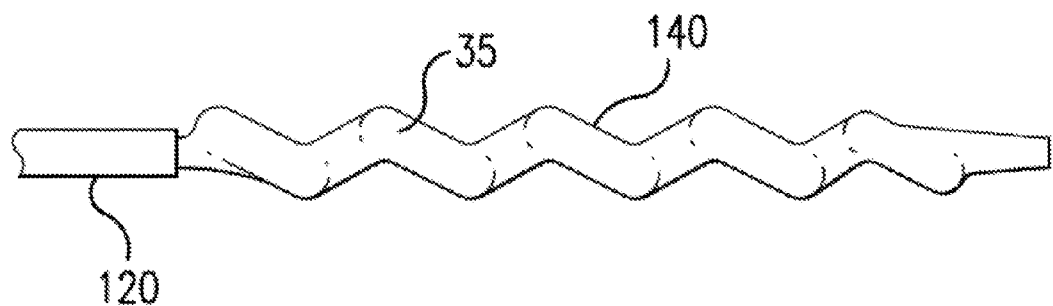
FIG. 7A AND FIG. 7B are schematic side views of different embodiments of the expandable member, in accordance with embodiments of the disclosed subject matter.
Figure 7B:
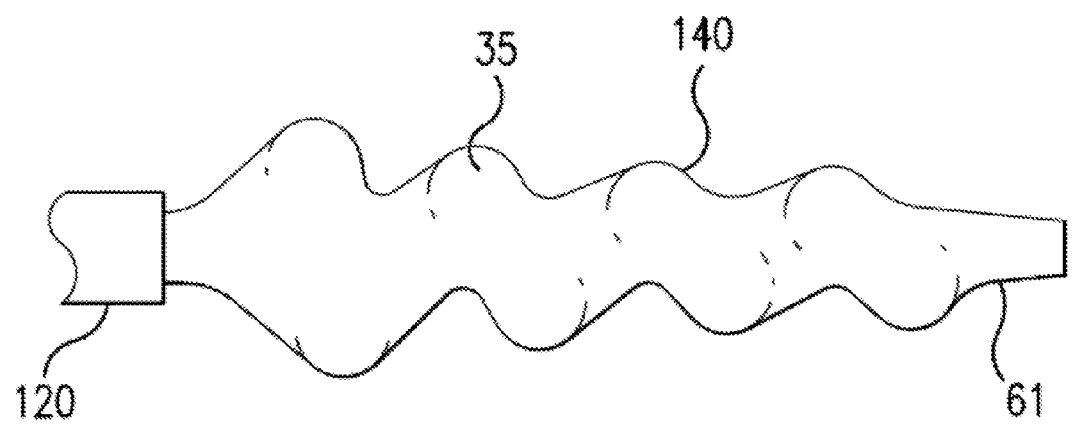

For example, and in accordance with one embodiment, the expandable member can include a cylindrical shape along a portion of the working length in the inflated configuration. In further embodiments, the balloon can have other suitable shapes, such as non-cylindrical, as discussed in more details in PCT/US2011/052018, which is incorporated by reference herein in its entirety. For example, the expandable member can have a generally spiral or helical shape about a longitudinal axis of the catheter when the expandable member is in the inflated configuration, as depicted in FIG. 7A and FIG. 7B.

For purpose of explanation and illustration, and not limitation, FIGS. 8A-8D depict a schematic view of expandable member having a frustoconical, generally conical, or tapered shape in the inflated condition, with the narrower end located at the distal end of the expandable member. The outer diameter of the expandable member of this embodiment increases toward the proximal end of the expandable member. In this manner, the overall diameter of the expandable member when inflated can be selected depending upon the exposed length of the expandable member. That is, by retraction of the outer tubular member 120, as described further below, the outer diameter of the expandable member is adjustable based upon the selected exposed length of the expandable member. For example, if the outer diameter is approximately 6 mm at the proximal end and decreases to about 2 mm at the distal end of the balloon, then the overall diameter would be about 4 mm at the proximal end if only half the working length is exposed. The overall diameter of the expandable member is thus selected as the maximum diameter of the exposed length.

Figure 8A:
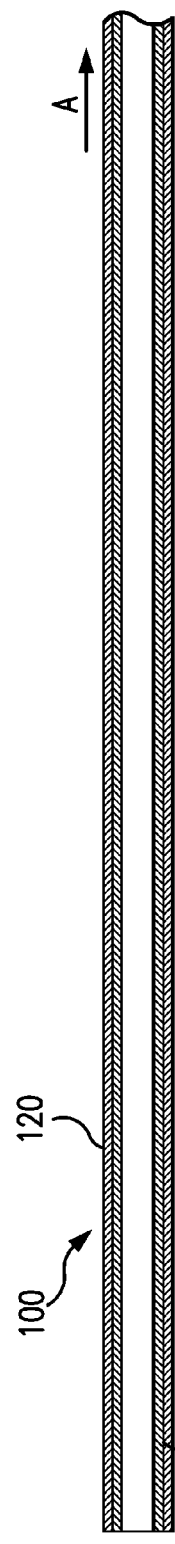
FIGS. 8A-8D are schematic images of a catheter in accordance with embodiments of the disclosed subject matter with the retractable outer tubular member selectively positioned to expose various lengths and corresponding diameters of the expandable member.
Figure 8B:
Figure 8C:
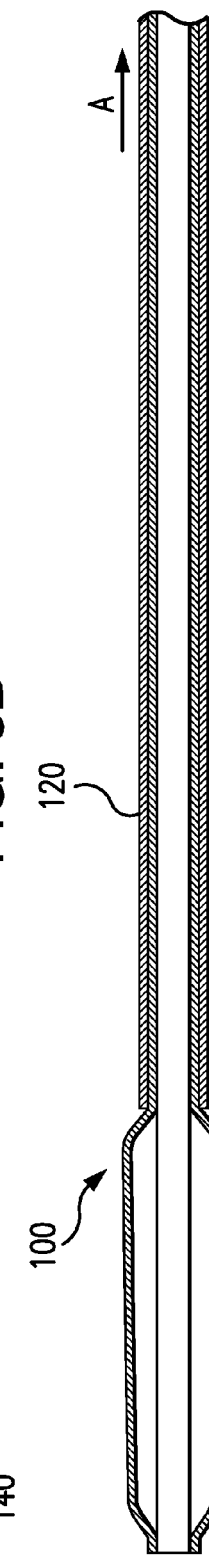
Figure 8D:
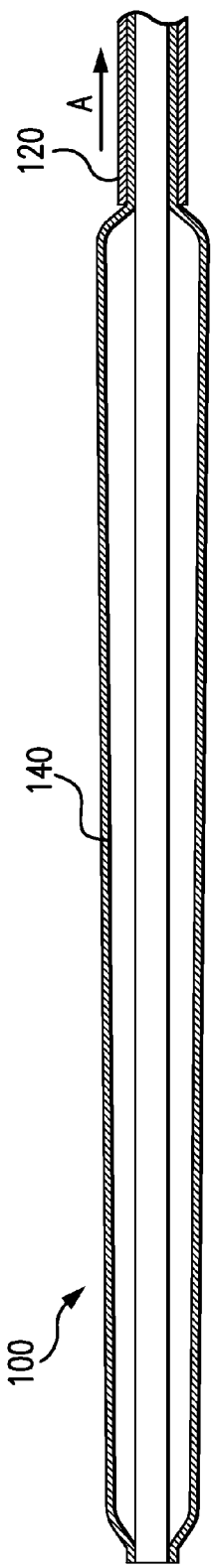

FIG. 8A shows the outer tubular member 120 completely extended in the extended position. FIGS. 8B and 8C show the outer tubular member selectively positioned in retracted positions to expose various lengths and diameters of the expandable member. In this embodiment, as the outer tubular member is retracted, the expandable member increases in diameter in the inflated configuration due to the conical configuration of the expandable member. FIG. 8D shows the outer tubular member further retracted. The length of the expandable member can vary depending upon the desired application and intended use. The length and diameter of the expandable member can thus be adjusted by selectively retracting the outer tubular member. Those skilled in the art will recognize that the expandable member can be formed in various different shapes and sizes which are not shown without departing from the scope of the disclosed subject matter.

Although not illustrated, the balloon of the disclosed subject matter can have a folded non-inflated configuration with wings wrapped around the balloon to form a low profile configuration for introduction and advancement within a patient's body lumen. As a result, the balloon inflates to a nominal working diameter by unfolding and filling the molded volume of the balloon. In accordance with another aspect of the disclosed subject matter, the expandable member can be configured relative the outer tubular member so as not to be completely exposed the entire length of the expandable member. In this manner, the proximal end of the expandable member will not be exposed when the outer tubular member is fully retracted as described further below, so as to allow the outer tubular member to be moved or returned distally relative to the inner tubular member. Thus, a folded balloon configuration can be used for the expandable member. For example, when the outer tubular member is in the extended configuration and positioned over the expandable member, the expandable member is in a folded arrangement within the outer tubular member. As the outer tubular member is retracted and the expandable member is inflated, the working length of the expandable member is no longer folded. However, a proximal portion of the expandable member will remain within the outer tubular member with the proximal portion folded within the outer tubular member. The folded proximal portion of the expandable member thus facilitates refolding of the expandable member after the expandable member is deflated and the outer tubular member is moved distally.

For purpose of example, the catheter and method as disclosed herein for refolding can be used for relatively long balloon lengths, such as peripheral balloons. In one embodiment, for purpose of example, the expandable member is a long balloon and has a length of approximately 220 mm. The approximate maximum working length of the expandable member can be approximately 200 mm, whereas the approximate folded proximal portion of the expandable member can be approximately 20 mm. Likewise, the refolding technique can be used with an expandable member having a short length, such as approximately 120 mm. In this embodiment, the maximum working length of the expandable member can be approximately 100 mm and the approximate folded proximal portion remaining in the outer tubular member can be approximately 20 mm.

To prevent the outer tubular member from being retracted beyond the desired working length, a stop mechanism can be employed. For example, but not limitation, the distal end of the catheter luer or other member configured to abut the proximal end of the outer tubular member prevent further movement of the outer tubular member with the proximal end of the expandable member still partially covered by the distal end of the outer tubular member.

The expandable member can be formed of a variety of suitable materials. A wide variety of suitable materials can be used for the expandable member in accordance with the disclosed subject matter. For example, the expandable member can be made from polymeric material, including compliant, semi-compliant, or non-compliant polymeric material or polymeric blends.

In one embodiment, the polymeric material is a polyamide/polyether block copolymer (commonly referred to as PEBA or polyether-block-amide). The polyamide and polyether segments of the block copolymers can be linked through amide or ester linkages. The polyamide block can be selected from various aliphatic or aromatic polyamides known in the art. Some non-limiting examples of an aliphatic include nylon 12, nylon 11, nylon 9, nylon 6, nylon 6/12, nylon 6/11, nylon 6/9, and nylon 6/6. In one embodiment, the polyamide is nylon 12. The polyether block can be selected from various polyethers known in the art. Some non-limiting examples of polyether segments include poly (tetramethylene ether), tetramethylene ether, polyethylene glycol, polypropylene glycol, poly(pentamethylene ether) and poly(hexamethylene ether). Commercially available PEBA material can also be utilized such as for example, PEBAX® materials supplied by Arkema (France). Additionally balloon grillamid can be used as the material for the expandable member. Various techniques for forming a balloon from polyamide/polyether block copolymer are known in the art. One such example is disclosed in U.S. Pat. No. 6,406,457 to Wang, the disclosure of which is incorporated by reference in its entirety.

In another embodiment, the expandable member is formed from polyamides. The polyamide can have substantial tensile strength, is resistant to pin-holing even after folding and unfolding, and is generally scratch resistant, such as those disclosed in U.S. Pat. No. 6,500,148 to Pinchuk, the disclosure of which is incorporated herein by reference in its entirety. Some non-limiting examples of polyamide materials suitable for the balloon include nylon 12, nylon 11, nylon 9, nylon 69 and nylon 66. Other suitable materials for constructing non-compliant balloons are polyesters such as polyethylene terephthalate) (PET), Hytrel thermoplastic polyester, and poly(ethylene.

In another embodiment, the balloon is formed of a polyurethane material, such as TECOTHANE® (Thermedics). TECOTHANE® is a thermoplastic, aromatic, polyether polyurethane synthesized from methylene disocyanate (MDI), polytetramethylene ether glycol (PTMEG) and 1,4 butanediol chain extender. TECOTHANE® grade 1065D can be used and has a Shore durometer of 65D, an elongation at break of about 300%, and a high tensile strength at yield of about 10,000 psi. However, other suitable grades can be used, including TECOTHANE® 1075D, having a Shore D hardness of 75. Other suitable compliant polymeric materials include ENGAGE® (DuPont Dow Elastomers (an ethylene alpha-olefin polymer)) and EXACT® (Exxon Chemical), both of which are thermoplastic polymers. Other suitable compliant materials include, but are not limited to, elastomeric silicones, latexes, and urethanes.

The compliant material can be cross linked or uncrosslinked, depending upon the balloon material and characteristics required for a particular application. The polyurethane balloon materials are not crosslinked. However, other suitable materials, such as the polyolefinic polymers ENGAGE® and EXACT®, can be crosslinked. By crosslinking the balloon compliant material, the final inflated balloon size can be controlled. Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure, and thereby avoid over expanding the balloon to an undesirably large diameter.

In another embodiment, the balloon is formed from a low tensile set polymer such as a silicone-polyurethane copolymer. The silicone-polyurethane can be an ether urethane and more specifically an aliphatic ether urethane such as PURSIL AL 575A and PURSIL AL10, (Polymer Technology Group), and ELAST-EON 3-70A (Elastomedics), which are silicone polyether urethane copolymers, and more specifically, aliphatic ether urethane cosiloxanes. In an alternative embodiment, the low tensile set polymer is a diene polymer. A variety of suitable diene polymers can be used such as, but not limited to, an isoprene such as an AB and ABA poly-styrene-black-isoprene), a neoprene, an AB and ABA poly (styrene-block-butadiene) such as styrene butadiene styrene (SBS) and styrene butadiene rubber (SBR), and 1,4-polybutadiene. In one embodiment, the diene polymer is an isoprene including isoprene copolymers and isoprene block copolymers such as poly(styrene-block-isoprene).

In one embodiment, the isoprene is a styrene-isoprene-styrene block copolymer, such as Kraton 1161K available from Kraton, Inc. However, a variety of suitable isoprenes can be used including HT 200 available from Apex Medical, Kraton R 310 available from Kraton, and isoprene (i.e., 2-methyl-1,3-butadiene) available from Dupont Elastomers. Neoprene grades useful in the disclosed subject matter include HT 501 available from Apex Medical, and neoprene (i.e., polychloroprene) available from Dupont Elastomers, including Neoprene G, W, T and A types available from Dupont Elastomers. Examples of other balloon and catheter embodiments which can be employed in accordance with the disclosed subject matter include U.S. Pat. Nos. 4,748,982; 5,496,346; 5,626,600; 5,300,085; and 6,406,457 and application Ser. Nos. 12/371,426; 11/539,944; and 12/371,422, each of which is hereby incorporated by reference in its entirety.

In accordance with another aspect of the disclosed subject matter, the expandable member is a balloon having a multilayer construction. The multilayer construction can include at least a first layer and a second layer having a combined wall thickness. As embodied herein, for purpose of illustration and not limitation, the first layer is made of a first polymer material having a first maximum blow-up-ratio, and the second layer is made of a second polymer material having a second maximum blow-up-ratio greater than the first maximum blow-up-ratio. The at least first and second layers define a compliance less than that of a single layer made of the first polymer material with a wall thickness equal to the combined wall thickness.

A multilayered balloon of the disclosed subject matter can be formed in whole or in part of coextruded polymeric tubular layers, and provides for ease of manufacture of the balloon and balloon catheter formed therefrom. The multilayered balloon is typically formed by conventional blow-molding in which a multilayered polymeric tube is radially expanded within a balloon mold. The resulting multilayered balloon has an inflated shape which corresponds to the inner surface of the mold and which has a diameter about equal to the inner diameter of the balloon mold, commonly referred to as the balloon's nominal working diameter. The nominal pressure is the inflation pressure required to fill the balloon to the nominal working diameter. In accordance with the disclosed subject matter, the balloon expands a very small amount (i.e., noncompliantly) at pressures above the nominal pressure. As a result, the balloon minimizes injury to a patient's blood vessel, which can otherwise occur if the balloon continues to expand a substantial uncontrolled amount at increasing inflation pressures above nominal. In one embodiment, the polymeric material of the first layer and the polymeric material of the second layer of the multilayered balloon are elastomers, which typically have a lower flexural modulus than nonelastomers. Elastomeric polymers suitable for forming the first and/or second layer of the multilayered balloon typically have a flexural modulus of about 40 kpsi to about 110 kpsi. Thus, unlike nonelastomeric materials such as PET, the multilayered noncompliant balloon of the disclosed subject matter can be formed of one or more elastomers which provide for improved balloon flexibility.

Additional details and examples of suitable multilayer balloons for use in the disclosed subject matter are described in U.S. Pat. No. 7,828,766, the contents of which is incorporated herein in its entirety.

In a further embodiment, the proximal end portion of the expandable member can include a reinforced proximal sleeve. The reinforced proximal sleeve can assist in resisting puncture of the expandable member, such as if the expandable member is to be inflated and deflated a number of times. The reinforced proximal sleeve can further protect the expandable member from the outer tubular member including any reinforcement of the outer tubular member if provided. The distal edge of the reinforced proximal sleeve can include a radiopaque material or have a suitable density to allow for radiopacity. The reinforced proximal sleeve also can prevent trumpeting effects of the outer tubular member and can reduce the kink stress along the expandable member. The reinforced proximal sleeve can also allow for refolding of the folded arrangement of the expandable member within the outer tubular member. The compliance of the balloon should be understood to refer to the degree to which the polymeric wall of the balloon stretches/distends as the balloon expands beyond the nominal diameter of the balloon. The compliance curve expresses the balloon outer diameter as a function of increasing inflation pressure in millimeters/atmospheres (mm/atm), so that a steeper curve or section of the curve indicates a higher compliance than a flatter curve. The term "noncompliant", should be understood to mean a balloon with compliance of not greater than about 0.03 mm/atm, and in one embodiment not greater than about 0.025 mm/atm. In contrast, compliant balloons typically have a compliance of greater than about 0.045 mm/atm. A noncompliant balloon of the disclosed subject matter generally has a compliance above nominal of about 0.01 to about 0.02 mm/atm, for a 3.0 mm diameter balloon. The compliance of the balloon is typically about 25% to about 50% less than the compliance of a balloon with a similar wall thickness but made from 100% of the first (e.g., highest durometer) material.

As previously noted, and in accordance with the discussed subject matter, the adjustable balloon catheter allows for the delivery of beneficial or therapeutic agents within a body lumen, such as cardiovascular or peripheral systems. Particularly, the adjustable balloon catheter herein includes the beneficial agent release structure for release of beneficial agent therefrom when the outer tubular member is moved relative to inner tubular member to expose or deliver an exposed length of the expandable member. In this manner, the outer tubular member can protect the therapeutic agent during delivery of the catheter to the selected site. Additionally, the amount and location of drug released will be a function of the exposed length of the expandable member. For example, and as described with reference to the various embodiments herein, the beneficial agent release structure can be in the form of a fluid with one or more pore structures, or as a coating or reservoir disposed on an exterior surface of the expandable member. Furthermore, the expandable member can have a shape to deliver at least a portion of a compartment along the working length of the expandable member when in the inflated configuration, wherein the beneficial agent is in communication with the compartment. Reference will now be made to various embodiments of adjustable balloon catheters in accordance with the discussed subject matter for purpose of illustration and not limitations.

For example, FIG. 9 shows the distal end of an adjustable balloon catheter for the delivery of a beneficial agent in fluid form. As shown in FIG. 9, expandable member 140 is coupled to the distal end portion of the inner tubular member 110 and has an inner chamber 35 defined therein in fluid communication with inflation lumen 130. As previously discussed, the expandable member 140 is transitionable between a deflated configuration and an inflated configuration. The outer tubular member 120 is selectively positioned between the extended position and the retracted position to define an exposed length of the working length of the expandable member 140. The embodiment of FIG. 9 depicts the expandable member 140 in the inflated configuration with an exposed length as defined by the retraction of outer tubular member 120, for purposes of illustration.

The expandable member 140 further includes an exterior surface along a working length thereof with at least one pore structure 141 defined therein in fluid communication with the inner chamber 35. Fluid from the inflation lumen 130 enters the inner chamber 35 of the expandable member 140 to expand the expandable member 140 into the inflated configuration. The at least one pore structure 141 is configured to permit fluid to exit therefrom when the expandable member 140 is in the inflated configuration and the outer tubular member 120 is retracted proximal to expose at least a portion of the pore structure 141. Additionally, and alternatively, the pore structure 141 can be configured to open when the expandable member 140 is in the inflated configuration. In this embodiment, the fluid can comprise beneficial or therapeutic drugs or agents. A source of beneficial agent therefore can be provided in fluid communication with the inflation lumen 130.

FIG. 10 depicts another embodiment of the distal end of an adjustable balloon catheter for delivery of beneficial agent. In this embodiment, a separate fluid lumen and chamber is provided for delivery of the therapeutic agent separate from the inflation fluid. For example, and with reference to a coaxial arrangement for the catheter shaft as depicted in cross section in FIG. 11A, the inner tubular member 110 can include at least an inflation lumen 130 and a fluid lumen 132. In this embodiment, the inner tubular member 110 includes a first inner tubular member 110' and a second inner tubular member 110" disposed therein. The second inner tubular member 110" thus defines the inflation lumen 130 and the annular space between the first inner tubular member 110' and the second inner tubular member 110" defines the fluid lumen 132 wherein each lumen extends along at least the distal end portion of the inner tubular member 110. FIG. 11A is a cross sectional view of the inner tubular member 110 of FIG. 10 taken along line 11-11. For purpose of illustration only, the outer tubular member 120 and the expandable member 140 are not shown in FIG. 11A. As depicted herein, the inflation lumen 130 can likewise be configured to receive a guidewire therein, wherein a seal is provided to prevent fluid flow of the inflation fluid from the distal end. Alternatively, the inner tubular member 110 can further include a guidewire lumen 150, which extends along at least the distal end portion of the inner tubular member 110. With reference to FIG. 11A, the guidewire lumen 150 would be annularly positioned within the inflation lumen 130, wherein the inflation lumen 130 is annularly positioned within the fluid lumen 132. As previously discussed, the guidewire lumen 150 permits the catheter 100 to be delivered over a guidewire while the inflation lumen 130 defines a pathway for fluid to travel along the inner tubular member 110 to inflate and deflate the expandable member 140 via the inner chamber 35. In addition to the inflation lumen 130 and the guide wire lumen 150, the fluid lumen 132 is provided to define a separate pathway or conduit for fluid such as beneficial agent to travel along the inner tubular member 110 and exit the expandable member 140.

As an alternative to a coaxial arrangement for the catheter shaft, FIG. 11B depicts an alternate embodiment of the cross section of the inner tubular member 110 taken along line 11-11 in which the catheter shaft is a monolithic structure with a multilumen arrangement, similar to FIG. 3. For purpose of illustration only, the outer tubular member 120 and the expandable member 140 are not shown in FIG. 11B. For example, but not limitation, the inner tubular member 110 can be a monolithic member with inflation lumen 130, fluid lumen 132, and guidewire lumen 150, defined therein. Thus, as depicted, the guidewire lumen 150, the fluid lumen 132, and the inflation lumen 130 extend parallel with and/or adjacent to each other.

With reference again to FIG. 10, the expandable member 140 of this embodiment can further include an inner membrane 140A and an outer membrane 140B. The inner membrane 140A and the outer membrane 140B can extend along at least a portion of the longitudinal length of the catheter. As depicted, the inner membrane 140A and the outer membrane 140B define a fluid chamber 135 therebetween, wherein the fluid chamber 135 is in fluid communication with the fluid lumen 132 to allow fluid from the fluid lumen 132 to enter the fluid chamber 135. The outer membrane 140B can include the at least one pore structure 141 defined therein. The pore structure 141 is configured to permit fluid to exit therefrom when the expandable member 140 is in the inflated configuration and the outer tubular member 120 is retracted proximal to at least a portion of the pore structure 141. For example, the pore can be configured to be closed or sealed when the expandable member is in the deflated configuration, and then stretched to open when in the inflated configuration.

The pore structure 141 can include a plurality of pores defined in the exterior surface of the outer membrane 140B. Each pore can be directly and/or independently in fluid communication with a fluid lumen, or can be in fluid communication with each other via the fluid chamber 135, if provided. For example, in the embodiment of FIG. 10, the pore structure 141 includes pores 141A-141H. The plurality of pores can have any suitable shape and size, and any desired number of pores can be provided. In one embodiment, the plurality of pores are substantially similar in size. In another embodiment, the plurality of pores vary in size such that pores of greater size generally will release a greater amount of fluid or agent therefrom. The plurality of pores can be arranged in a pattern along the expandable member 140. The pattern can be uniform along the working length of the expandable member 140 or alternatively, non-uniform to provide a varied gradient as desired.

As discussed further below, the catheter according to the subject matter can also include markers. For example, and as depicted in FIG. 10, the inner tubular member 110 can include a distal radiopaque marker 63 proximate the distal end portion thereof. The inner tubular member 110 can further include at least one proximal marker 75 spaced proximally from the distal marker 63. FIG. 10 depicts a plurality of proximal markers 75 spaced a predetermined distance apart along the inner tubular member 110 and along the working length of the expandable member 140. The plurality of pores can have a pattern associated with the plurality of proximal markers. For example, in the embodiment of FIG. 10, each set of pores 141A and 141E, 141B and 141F, 141C and 141G, and 141D and 141H, is associated with a respective radiopaque marker 75 along the length of the inner tubular member 110. As such, the desired pores or locations for the release of agent therefrom can be selected by adjustment of the outer tubular member relative the inner tubular member.

Further in accordance with another aspect of the disclosed subject matter, the exterior surface of the expandable member can define at least a portion of a compartment when in the inflated configuration. For example, and without limitation, FIG. 12 depicts another embodiment of the distal end of the adjustable balloon catheter. The exterior surface of the expandable member 140 can define at least one compartment along the working length of the expandable member when in the inflated configuration. That is for illustration and not limitation, the exterior surface of the expandable member 140 defines at least a portion of a compartment $C_1$ along the working length of the expandable member 140 when in the inflated configuration. FIG. 12 depicts compartments $C_1$, $C_2$, and $C_3$ along the exposed portion of the working length of the expandable member 140. A select number of compartments of the expandable member can likewise remain housed within the outer tubular member 120 if desired by selective retraction of the outer member. The retraction of the outer tubular member 120 in the proximal direction therefore can determine the number of compartments exposed for the working length of the expandable member 140. As depicted in FIG. 12, the pore structure 141 includes at least one pore 141J in fluid communication with the at least one compartment $C_3$. In other embodiments, the port structure 141 can include a plurality of pores in fluid communication with the at least one compartment. In this manner, therapeutic agent can be introduced into the compartment when the balloon inflates against the tissue T of a vessel wall.

The expandable member 140 can comprise any suitable shape to provide separate compartments as desired. For purposes of illustration and example, as depicted in FIG. 12, the exterior surface of the exposed length of the expandable member 140 has a generally sinusoidal shape along a longitudinal axis of the catheter in the inflated configuration. Alternatively, the separate compartments can be defined by cylindrical or conical portions of varied or alternating diameter.

In accordance with another embodiment, the separate compartments can be defined by a plurality of expandable members spaced longitudinally along the distal end portion of the inner tubular member. In particular, FIG. 13 depicts an embodiment of the distal end of the adjustable balloon catheter in partial cross-section having a plurality of expandable members 140, 140C, 140D, 140E. In this embodiment, at least a second expandable member 140C is coupled to the distal end portion of the inner tubular member 110 proximate the first expandable member 140. The second expandable member 140C further includes an inner chamber 35C defined therein in fluid communication with the inflation lumen 130 via inflation port 601. The second expandable member 140C has an exterior surface defining a portion of compartment $C_1$ and further defines another portion of compartment $C_2$. Thus, each expandable member can define more than one compartment. Each compartment can include a pore structure 602 with at least one pore in fluid communication with the respective compartment and the fluid lumen 132. In other embodiments, the pore structure can include a plurality of pores in fluid communication with the at least one compartment.

The plurality of expandable members independently or together can have a variety of suitable shapes. As depicted in FIG. 13, the plurality of expandable members 140, 140C, 140D, 140E collectively have a sinusoidal shape when inflated. As depicted, therapeutic agent can be introduced into the compartments defined by the plurality of expandable members when the members inflates against the tissue T of a vessel wall.

Figure 14:
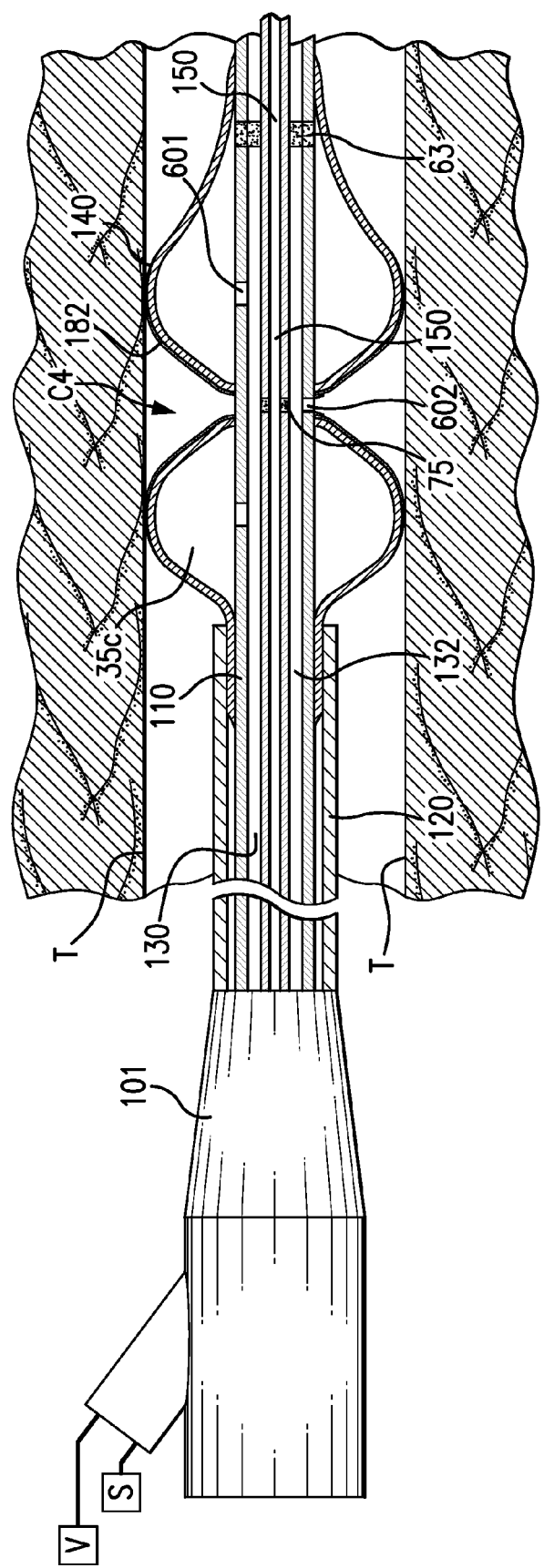
FIG. 14 is a cross-sectional view of an adjustable balloon catheter, according to another embodiment of the disclosed subject matter.

As previously noted, the beneficial agent release structure is not limited to a pore structure, but can include other embodiments as desired. For example, and according to another embodiment as depicted in FIG. 14, the exterior surface of the expandable member 140 can have a beneficial agent release structure associated therewith in communication with a compartment $C_4$. The beneficial agent release structure can include a coating 182 of beneficial agent disposed on the exterior surface of the expandable member 140 proximate the compartment $C_4$. Alternatively or in addition thereto, the beneficial agent release structure can include at least one reservoir (not shown) defined in the exterior surface of the expandable member 140 to retain therapeutic agent proximate compartment $C_4$. Additionally, or alternatively, the beneficial agent release agent can be in the form of microcapsules or spheres provided on the surface in communication with compartment $C_4$.

As previously noted, and as shown in FIG. 14, the inner tubular member of the adjustable catheter discussed herein can further include a fluid lumen 132 defined therein and extending from the proximal end portion of the inner tubular member 110 to the distal end portion of the inner tubular member 110. The fluid lumen 132 be in fluid communication with the compartment $C_4$ via the pore structure 602.

As depicted in FIG. 14, when the expandable member 140 is in the inflated condition and the outer tubular member 120 is retracted proximal to expose the compartment $C_4$, a beneficial agent can be introduced through the fluid lumen 132 and out the pore structure 602 into the compartment $C_4$. As depicted, the expandable member 140 abuts against the tissue T of a vessel wall in the inflated condition. A source of beneficial agent S can be in fluid communication with the fluid lumen for introduction of the beneficial agent therein. Furthermore, the pressure within compartment and thus against the vessel tissue can be controlled by adjusting the fluid flow through the fluid lumen and/or within the expandable member. In this manner, pressure within the compartment and against the vessel wall can be increased, decreased and/or oscillated as desired to control or enhance drug uptake into the vessel wall and tissue. Additionally, with the expandable member 140 in the inflated condition and the outer tubular member 120 retracted proximal to the at least one compartment $C_4$, a vacuum source V in fluid communication with the fluid lumen 132 can draw negative pressure in the compartment $C_4$. The negative pressure can likewise adjust pressure within the compartment, and/or extract beneficial agent S and other materials remaining in the compartment $C_4$.

As with the previous embodiments of FIG. 9 and FIG. 10, the pore structure 602 of FIG. 14 can include a plurality of pores defined in the exterior surface of the expandable member 140. The plurality of pores can be arranged in a pattern along the expandable member and can be a uniform pattern along the working length of the expandable member or can be a non-uniform pattern. The respective pores of the plurality of pores can have a suitable size. The pores can be substantially similar in size or can vary in size. The inner tubular member can further include a radiopaque distal marker 63 proximate the distal end portion that can act as a stop within the fluid lumen 132 and can further include at least one proximal marker 75 spaced proximally of the distal marker that can define a location of the pore structure 602.

The therapeutic agent can be any suitable drug or agent such as for the treatment of a disease. Examples of suitable beneficial or therapeutic agents include any suitable drug or agent, such as anti-proliferative, anti-inflammatory, antineoplastic, antiplatelet, anti-coagulant, anti-fibrin, antithrombotic, antimitotic, antibiotic, antiallergic and antioxidant compounds. Such therapeutic agents can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, and a retroviral vector.

For example, the beneficial or therapeutic agent can include a cytostatic drug. The term "cytostatic" as used herein means a drug that mitigates cell proliferation but allows cell migration. These cytostatic drugs, include for the purpose of illustration and without limitation, macrolide antibiotics, rapamycin, everolimus, zotaroliumus, biolimus, temsirolimus, deforolimus, novolimus, myolimus, structural derivatives and functional analogues of rapamycin, structural derivatives and functional analogues of everolimus, structural derivatives and functional analogues of zotarolimus and any marcrolide immunosuppressive drugs. The term "cytotoxic" as used herein means a drug used to inhibit cell growth, such as chemotherapeutic drugs. Some non-limiting examples of cytotoxic drugs include vincristine, actinomycin, cisplatin, taxanes, paclitaxel, and protaxel. Other drugs include dexamethasone, statins, sirolimus, and tacrolimus.

In addition to the beneficial or therapeutic agent, any of a variety of fluid compositions can be applied to or delivered from the expandable member. The fluid can include compounds or additives, such as polymers, binding agents, plasticizers, solvents, surfactants, additives, chelators, fillers, excipients, and the like, or combinations thereof. Suitable excipients, binding agents and other compartments include those described in detail in U.S. patent application Ser. No. 12/636,079, which is hereby incorporated by reference in its entirety. In one embodiment, excipients include poly(ethylene glycol) (PEG), polyvinylpyrrolidone (PVP), polyoxyethylene sorbitan monooleate (tweens), poloxamer triblock copolymers of poly(ethylene oxide)-poly(propylene oxide)-poly(ethylene oxide) (Pluronics), carboxymethyl cellulose (CMC), and PEG phospholipids such as 1,2-distearoyl-sn-glycero-3-phosphoethanolamine-N-(methoxy(polyethylene glycol)-2000) (PEG-PE). In one embodiment, plasticizers include PEG, propylene glycol, N-methylpyrrolidone (NMP), glycerin, and tweens. Examples of possible compounds include zotarolimus, PVP and glycerol. In one embodiment the beneficial or therapeutic agent can be provided in liquid form or dissolved in a suitable solvent. In another embodiment, the therapeutic agent is provided as a particulate and mixed in a suitable carrier for application as a fluid.

The fluid compositions, such as the beneficial or therapeutic agents, can be applied to the expandable member using a variety of know techniques, such as spraying (air-atomization, ultrasonic, electrostatic, piezoelectric, etc.), spray drying, pneumatic spray, spray with patterning, electrospinning, direct fluid application, dip-coating, spin-coating, pipette coating, syringe coating, vapor deposition, roll coating, micro-droplet coating, ultrasonic atomization, or other means as known to those skilled in the art. The coating can be applied over at least a length or the entirety of the expandable member. By way of example, and not limitation, certain coating processes that can be used with the instant disclosed subject matter are described in U.S. Pat. No. 6,669,980 to Hansen; U.S. Pat. No. 7,241,344 to Worsham; U.S. Publication No. 2004/0234748 to Stenzel; and U.S. Patent Application Ser. No. 61/345,575, the entire disclosures of which are hereby incorporated by reference. In accordance with one embodiment of the disclosed subject matter, the coating can be applied to either a folded or inflated balloon. Furthermore, the coating can be directly applied into the folds of the folded balloons. The coating characteristics are affected by process variables. For example, for dip-coating process, coating quality and thickness can vary as an effect of variables such as number, rate, and depth of dips along with drying time and temperature.

In accordance with another aspect of the disclosed subject matter, the expandable member can include microcapsules on its outer surface. In this regard, the microcapsules are configured to encompass the coating and/or therapeutic agent. Upon inflation of the expandable member the microcapsules located on the surface of the expandable member contact the tissue of the arterial wall. Alternatively, the microcapsules can be formed in the wall of the expandable member surface or on the tissue engaging member. The coating and/or therapeutic agent can be released from the microcapsules by fracturing of the microcapsules and/or diffusion from the microcapsule into the arterial wall. The microcapsules can be fabricated in accordance with the methods disclosed in U.S. Pat. No. 5,102,402 to Dror or U.S. Pat. No. 6,129,705 to Grantz and the patents referenced therein, each of which is incorporated herein by reference in its entirety.

In accordance with another aspect of the disclosed subject matter, the inner tubular member and/or the outer tubular member can each include a distal tip configuration.

Figure 15:
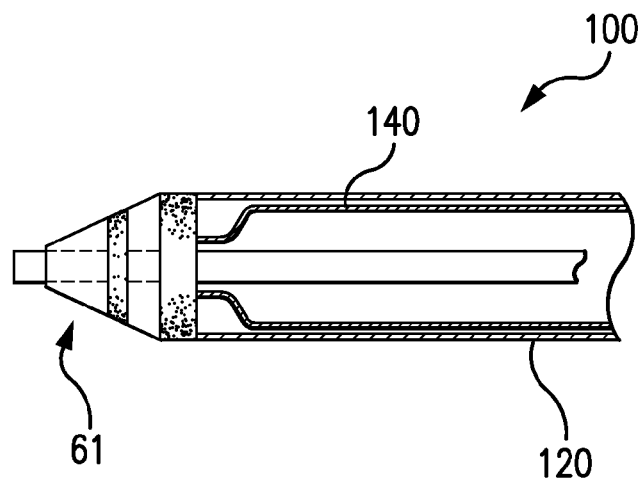
FIG. 15 and FIG. 16 are schematic views of the distal end section of a catheter with the outer tubular member in the extended position and the retracted position, respectively, wherein the outer tubular member has a distal marker, in accordance with an embodiment of the disclosed subject matter.
Figure 16:
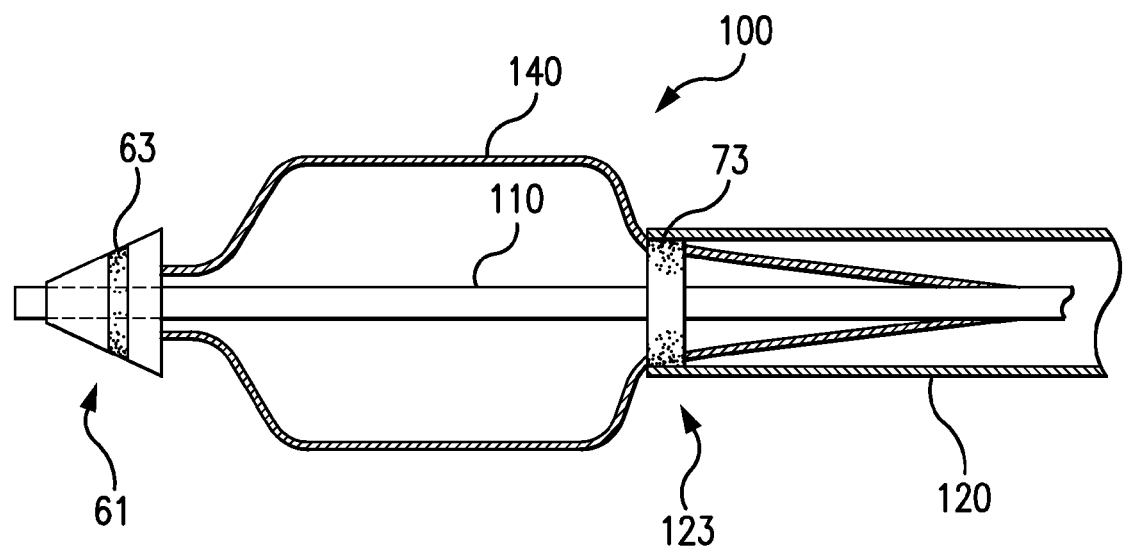

In accordance with another aspect of the disclosed subject matter referring to FIGS. 15 and 16, for purpose of illustration and not limitation, an embodiment of a balloon catheter in accordance with the disclosed subject matter is depicted in its delivery configuration with the outer tubular member fully extended, and in its expanded configuration with the outer tubular member retracted, respectively. The distal end 123 of the outer tubular member and the distal tip 61 of the inner tubular member each include a marker. The distal tip 61 of the inner tubular member can include a radiopaque marker 63 to enhance visibility of the distal tip within a patient's vasculature, as further described herein. The distance between the marker of the inner tubular member and marker of the outer tubular member when the outer tubular member is retracted indicates the working length of balloon that is exposed.

Alternatively or additionally, a scale or markers can be disposed on the proximal end of the catheter to aid in length adjustment and drug delivery, as further discussed herein. The distal tip can be constructed of a soft polymer material which includes tungsten as the marker. The soft tip can prevent damage to the vessel walls while the catheter is within a patient's vasculature.

Figure 17:
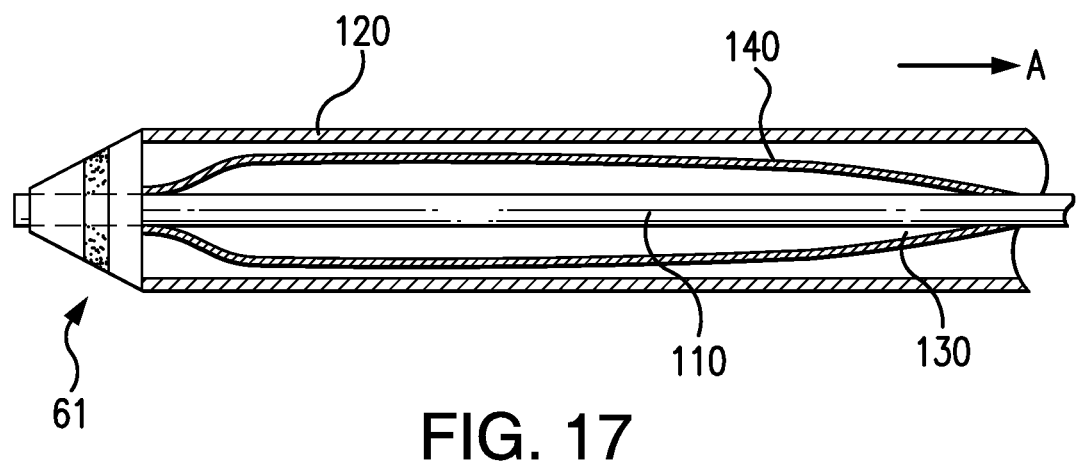
FIG. 17 and FIG. 18 are schematic side views in partial cross-section of embodiments of the distal tip of a catheter in the retracted position and in the extended position, respectively in accordance with the disclosed subject matter.
Figure 18:
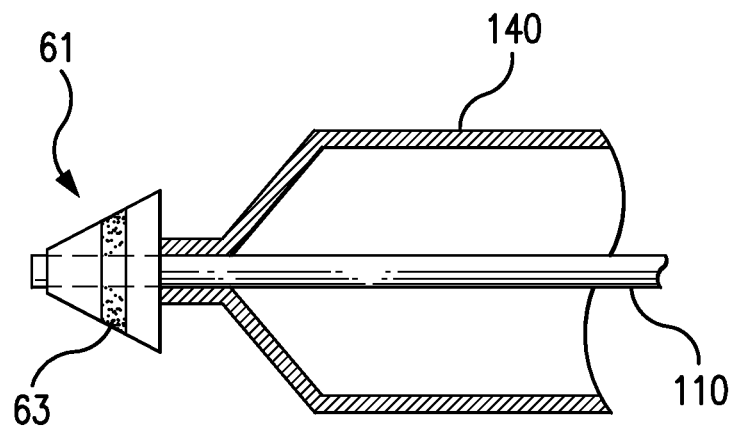

Further, for purpose of illustration and not limitation, FIG. 17 depicts the expandable member in a deflated configuration with the outer tubular member fully extended. In this embodiment, the outer tubular member does not include a tip and the outer tubular member does not include a marker at the distal end. In this embodiment, the distal tip of the inner tubular member is sized to engage against the outer tubular member and prevent over-extension of the outer tubular member distally. FIG. 18 depicts the expandable member in the inflated configuration with the outer tubular member retracted. The distal tip, as shown, also can provide a seal preventing or decreasing the exposure of the expandable member and therapeutic agent to the patient's blood until the catheter is at the treatment site and the outer tubular member is retracted. The distal tip as embodied herein also provides a smoother transition between the proximal end of the tip and the distal end of the outer tubular member. In another embodiment, the distal tip can be formed by rounding of the distal end of the inner tubular member.

Figure 19A:
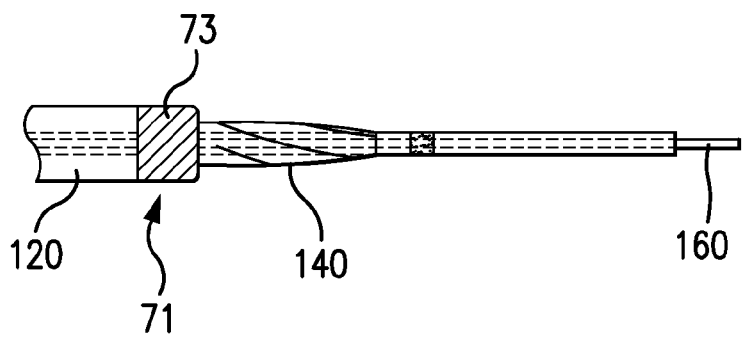
FIGS. 19A-19C are schematic images of alternate embodiments of distal tips of a catheter in accordance with the disclosed subject matter.
Figure 19B:
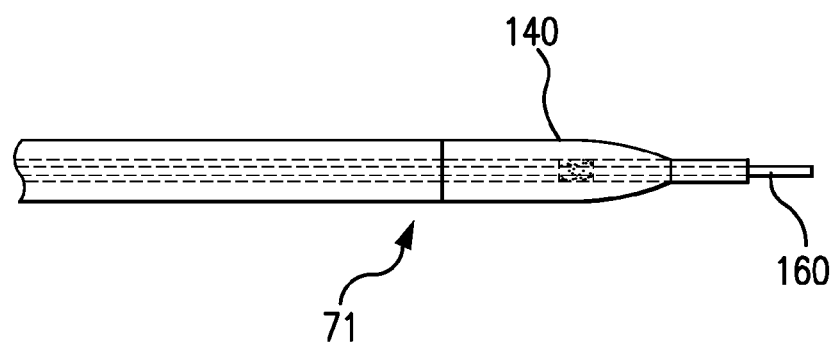
Figure 19C:
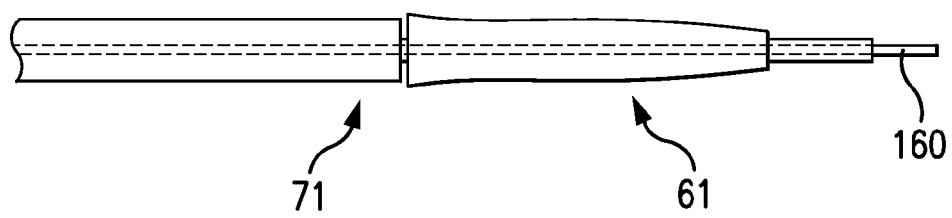

In another embodiment, the outer tubular member includes a distal tip at the distal end thereof. FIG. 19A depicts the distal tip 71 of the outer tubular member with a metal marker 73 on the distal end of the outer tubular member 120. In this embodiment, the inner tubular member 110 does not include a tip at a distal end thereof. FIG. 19B depicts the distal tip 71 of the outer tubular member wherein the distal end of the outer tubular member includes a soft tip with a marker. As discussed above, one method of achieving the depicted configuration is through the use of tungsten loaded polymers. In other embodiments of the disclosed subject matter, both the inner tubular member and the outer tubular member can include distal tips, respectively. FIG. 19C depicts the distal tip 61 of the inner tubular member and the distal tip 71 of the outer tubular member, both of which can include markers and can be soft at their respective distal ends. The tips of the inner tubular member and the outer tubular member can contribute to the stiffness or flexibility of the catheter, as previously discussed herein.

In accordance with one aspect of the disclosed subject matter, the adjustable balloon catheter 100 can include a plurality of radiopaque markers. The markers can be placed in a variety of suitable locations along the catheter including, but not limited to, the inner tubular member, the outer tubular member, and the expandable member.

Figure 20:
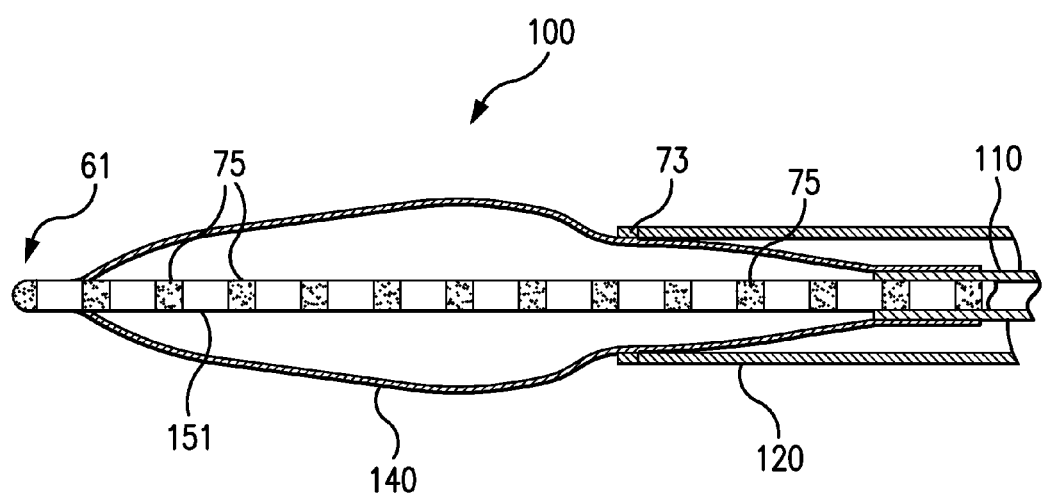
FIG. 20 is a schematic cross-sectional side view of the distal end of the catheter having gradient markers in accordance with another embodiment of the disclosed subject matter.

Reference is made to FIG. 20 for purpose of illustration and not limitation, which depicts an embodiment of the distal end of the adjustable balloon catheter. FIG. 20 depicts a plurality of markers distributed along the adjustable length catheter. The distal tip 61 of the inner tubular member includes a radiopaque marker 63. Further, as shown, the inner tubular member includes at least one proximal marker proximal to the distal marker. In the embodiment of FIG. 20, radiopaque markers extend from the distal end of the inner tubular member, along the length towards its proximal end. The markers 75 can extend along a portion of the inner tubular member within the expandable member. At least one proximal marker can be located proximate a center of the working length of the expandable member. The markers can continue to the proximal end of the inner tubular member including markers on the hypotube, if provided. In this embodiment, the outer tubular member includes a marker 73 at the distal end thereof. The marker 73 can be positioned at a tip of the outer tubular member or independent of any tip at the outer tubular member. In embodiments where the inner tubular member includes a coiled construction a radiopaque marker can be provided with the coiled construction or at least a portion of the coiled construction can be made of radiopaque material. The marker in this embodiment can be a separate radiopaque member attached to the member, or can be applied by any suitable method, including but not limited to, a vapor depositing process, as known in the industry.

In one embodiment, the radiopaque markers are strategically spaced a predetermined distance apart from each other to gauge the working length of the expandable member. The markers are spaced at known increments from each other allowing a physician to determine the exact length of the expandable member that is exposed and to determine the location of other portions of the catheter. For example, each radiopaque marker can be spaced approximately 10 mm apart along a portion of the inner tubular member. Additionally, or alternatively, gradients or similar indicia can provided on the proximal end of the adjustable balloon catheter to identify the distance in which the outer tubular member has been retracted and thus the exposed length of the expandable member.

Figure 21:
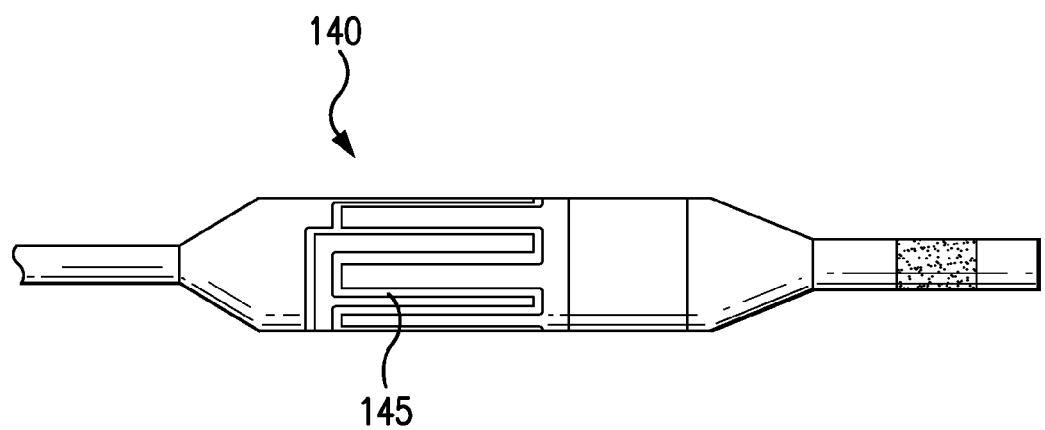
FIG. 21 is a schematic side view of a distal end of the catheter with the expandable member with an alternative marker arrangement, in accordance with an embodiment of the disclosed subject matter.

The expandable member can also include markers. The markers can be positioned at a plurality of suitable locations, including, but not limited to, the distal end of the expandable member and the proximal end of the expandable member. In one embodiment, a radiopaque marker 145 is applied to the exterior of the expandable member with a pattern to define a length, diameter or other characteristic when inflated, as depicted in FIG. 21. The marker in this embodiment can be applied by a vapor depositing, as known in the industry.

The markers can include any suitable material. For example, the markers can be constructed of a polymer filled or impregnated with a radiopaque material and can further include, but not limited to, PPS, Tungsten, and glass fiber combination; PA12 and ceramics combination; PEEK and ceramics combination; and a PBT and ceramics combination.

As understood from the description above, the disclosed subject matter includes methods of deploying a medical device, and providing an adjustable balloon. The method includes providing an adjustable balloon catheter including any of a combination of the features as previously described. The method further includes inserting the catheter into a body lumen of a patient and retracting the outer tubular member in a proximal direction to define the exposed length of the working length of the expandable member. The retracting can further include selecting the exposed length of the expandable member such that an outer diameter of the expandable member is selectively determined by the outer tubular member. The exposed length of the expandable member is inflated to the inflated configuration, such as by introducing fluid into the inflation lumen. The expandable member is deflated to the deflated configuration and withdrawn from the body lumen of a patient.

Accordingly, a physician can selectively expose as much of the balloon as needed in order to perform the desired treatment. Thus, in accordance with the disclosed subject matter, a physician can treat a vascular section of varying length using an expandable member or balloon of one length by selectively exposing the desired length described above for the purpose of illustration and not limitation. The additional aspects and benefits of the method performed using the catheter as disclosed are evident and described in detail in conjunction with the various features of the device.

In accordance with another aspect of the disclosed subject matter, a method of delivering a beneficial agent is provided. The method includes providing an adjustable balloon catheter of any of the embodiments discussed herein. In one particular embodiment and with reference again to FIG. 14, the adjustable balloon catheter includes an inner tubular member 110 having a proximal end portion, a distal end portion, and a length therebetween. The inner tubular member 110 further has an inflation lumen 130 and a fluid lumen 132 defined therein. An expandable member 140 is coupled to the distal end portion of the inner tubular member 110 and has an inner chamber 35 defined therein in fluid communication with the inflation lumen 130. The expandable member 140 is transitionable between a deflated configuration and an inflated configuration.

As shown in FIG. 14, the expandable member 140 further has an exterior surface along a working length thereof, the exterior surface defining at least one a portion of a compartment $C_4$ along the working length of the expandable member when in the inflated configuration. The exterior surface further has a beneficial agent release structure associated therewith in communication with the at least one compartment $C_4$. An outer tubular member 120 is movable relative to the inner tubular member 110, the outer tubular member 120 including a distal end. The outer tubular member 120 is moveable between an extended position disposed over the expandable member 140 and a retracted position proximal to the extended position, the outer tubular member 120 being selectively positioned between the extended position and the retracted position to define an exposed length of the working length of the expandable member 140.

The method further includes retracting the outer tubular member 120 in a proximal direction to define the exposed length of the working length of the expandable member 140 and inflating the exposed length of the expandable member 140 to the inflated configuration. The beneficial agent is released from the at least one pore structure to form a reservoir and the expandable member 140 is deflated to the deflated configuration.

Alternatively, in accordance with another aspect of the disclosed subject matter, a method of delivering a beneficial agent using another one of the adjustable balloon catheters discussed herein is provided. For example, the method can, comprise providing an adjustable balloon catheter including an inner tubular member having a proximal end portion, a distal end portion, and a length therebetween. The inner tubular member can further have an inflation lumen and a fluid lumen defined therein. An expandable member is coupled to the distal end portion of the inner tubular member and has an inner chamber defined therein in fluid communication with the inflation lumen, the expandable member transitionable between a deflated configuration and an inflated configuration. The expandable member further has an exterior surface along a working length thereof, the exterior surface having at least one pore structure defined therein in fluid communication with the fluid lumen. An outer tubular member is movable relative to the inner tubular member, the outer tubular member including a distal end, the outer tubular member being moveable between an extended position disposed over the expandable member and a retracted position proximal to the extended position. The outer tubular member is selectively positioned between the extended position and the retracted position to define an exposed length of the working length of the expandable member. The method further includes retracting the outer tubular member in a proximal direction to define the exposed length of the working length of the expandable member and inflating the exposed length of the expandable member to the inflated configuration. The method further includes releasing beneficial agent from the at least one pore structure and deflating the expandable member to the deflated configuration.

Further in accordance with another aspect of the disclosed subject matter, a method of delivering a beneficial agent using one of the adjustable balloon catheters discussed herein is provided. For example, the method can, comprise providing an adjustable balloon catheter including an inner tubular member having a proximal end portion, a distal end portion, and a length therebetween, the inner tubular member further having an inflation lumen and a fluid lumen defined therein. An expandable member is coupled to the distal end portion of the inner tubular member and having an inner chamber defined therein in fluid communication with the inflation lumen, the expandable member transitionable between a deflated configuration and an inflated configuration. The expandable member further has an exterior surface along a working length thereof, the exterior surface defining at least one a portion of a compartment along the working length of the expandable member when in the inflated configuration, the exterior surface further having a beneficial agent release structure associated therewith in communication with the at least one compartment. An outer tubular member is movable relative to the inner tubular member, the outer tubular member including a distal end, the outer tubular member being moveable between an extended position disposed over the expandable member and a retracted position proximal to the extended position, the outer tubular member being selectively positioned between the extended position and the retracted position to define an exposed length of the working length of the expandable member. The method further includes retracting the outer tubular member in a proximal direction to define the exposed length of the working length of the expandable member and inflating the exposed length of the expandable member to the inflated configuration with the compartment along the exposed length. The beneficial agent is released from the beneficial agent release structure into the compartment and the expandable member is deflated to the deflated configuration.

While the disclosed subject matter is described herein in terms of certain embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

Many modifications, variations, or other equivalents to the specific embodiments described above will be apparent to those familiar with the art. It is intended that the scope of this disclosed subject matter be defined by the claims below and those modifications, variations and equivalents apparent to practitioners familiar with this art Thus, it is intended that the disclosed subject matter include modifications and variations that are within the scope of the appended claims and their equivalents.

What is claimed is:

1. An adjustable balloon catheter comprising:
   an inner tubular member having a proximal end portion, a distal end portion, and a length therebetween, the inner tubular member further having an inflation lumen and a fluid lumen defined therein;
   at least one expandable member coupled to the distal end portion of the inner tubular member and having an inner chamber defined therein in fluid communication with the inflation lumen, the at least one expandable member transitionable between a deflated configuration and an inflated configuration by inflation medium from the inflation lumen, wherein the at least one expandable member is in fluid communication with the inflation lumen, the at least one expandable member further having an exterior surface along a working length thereof, the exterior surface defining at least a portion of a compartment along the working length when in the inflated configuration, the exterior surface having at least one beneficial agent release structure defined therein, the at least one beneficial agent release structure including at least one pore structure in fluid communication with the fluid lumen and in fluid communication with the compartment when in the inflated configuration;
   an outer tubular member movable relative to the inner tubular member, the outer tubular member including a distal end, the outer tubular member being moveable between an extended position disposed over the expandable member and a retracted position proximal to the extended position, the outer tubular member being selectively positioned between the extended position and the retracted position to define an exposed length of the working length of the at least one expandable member, wherein beneficial agent can be introduced through the fluid lumen and released out the at least one pore structure into the compartment when the at least one expandable member is in the inflated condition and the outer tubular member is retracted proximal to the compartment.

2. The adjustable balloon catheter according to claim 1, further comprising a fluid chamber defined between an inner membrane and an outer membrane of the at least one expandable member, the fluid chamber in fluid communication with the fluid lumen and the outer membrane having the at least one beneficial agent release structure defined therein.

3. The adjustable balloon catheter according to claim 1, further comprising a source of beneficial agent in fluid communication with the fluid lumen.

4. The adjustable balloon catheter according to claim 1, wherein the at least one pore structure includes a plurality of pores arranged in a pattern along the at least one expandable member.

5. The adjustable balloon catheter according to claim 4, wherein the pattern is uniform along the working length of the at least one expandable member.

6. The adjustable balloon catheter according to claim 4, wherein the plurality of pores are substantially similar in size.

7. The adjustable balloon catheter according to claim 4, wherein the plurality of pores vary in size.

8. The adjustable balloon catheter according to claim 1, wherein the inner tubular member includes a radiopaque distal marker proximate the distal end portion.

9. The adjustable balloon catheter according to claim 8, wherein the inner tubular member further includes at least one proximal marker spaced proximally from the distal marker.

10. The adjustable balloon catheter according to claim 9, wherein a plurality of proximal markers are spaced a predetermined distance apart on the inner tubular member along the working length of the at least one expandable member.

11. The adjustable balloon catheter according to claim 10, wherein the at least one beneficial agent release structure further includes a plurality of pores defined by the exterior surface of the at least one expandable member, the plurality of pores having a pattern associated with the plurality of proximal markers.

12. The adjustable balloon catheter according to claim 1, wherein the at least one expandable member has a generally spiral or helical shape about a longitudinal axis of the catheter when the at least one expandable member is in the inflated configuration.

13. The adjustable balloon catheter according to claim 1, wherein the at least one expandable member includes a first expandable member and a second expandable member coupled to the distal end portion of the inner tubular member proximate the first expandable member, the second expandable member having an inner chamber defined therein in fluid communication with the inflation lumen, the second expandable member further having an exterior surface defining another portion of the compartment.

14. The adjustable balloon catheter according to claim 1, wherein the exterior surface of the expandable member defines a plurality of compartments spaced along the working length of the at least one expandable member in the inflated configuration.

15. The adjustable length balloon catheter according to claim 14, wherein the exterior surface of the exposed length of the at least one expandable member has a generally sinusoidal shape along a longitudinal axis of the catheter in the inflated configuration.

16. The adjustable balloon catheter according to claim 1, wherein the inner tubular member further has a guidewire lumen defined therein, the guidewire lumen extending along at least the distal end portion of the inner tubular member.

17. The adjustable balloon catheter according to claim 16, wherein the guidewire lumen, the fluid lumen, and the inflation lumen are in a coaxial configuration.

18. The adjustable balloon catheter according to claim 16, wherein the guidewire lumen, the fluid lumen, and the inflation lumen extend parallel with each other.

19. An adjustable balloon catheter comprising:
  an inner tubular member having a proximal end portion, a distal end portion, and a length therebetween, the inner tubular member further having an inflation lumen defined therein;
  a first expandable member and a second expandable member coupled to the distal end portion of the inner tubular member and each having an inner chamber defined therein in fluid communication with the inflation lumen, wherein the second expandable member is proximate the first expandable member, the first and second expandable members transitionable between a deflated configuration and an inflated configuration by inflation medium from the inflation lumen, the first and second expandable members in fluid communication with the inflation lumen, the first and second expandable members each further having an exterior surface along a working length thereof, the exterior surface of the first expandable member defining at least a portion of a compartment along the working length of the first expandable member when in the inflated configuration and the exterior surface of the second expandable member defining at least a second portion of the compartment along the working length of the second expandable member when in the inflated configuration,
  at least one beneficial agent release structure associated with the compartment, the at least one beneficial agent release structure disposed between the first and second expandable members; and
  an outer tubular member movable relative to the inner tubular member, the outer tubular member including a distal end, the outer tubular member being moveable between an extended position disposed over the first and second expandable members and a retracted position proximal to the extended position, the outer tubular member being selectively positioned between the extended position and the retracted position to define an exposed length of the working length of at least one of the first and the second expandable members.

20. The adjustable balloon catheter according to claim 19, wherein the at least one beneficial agent release structure includes a coating of beneficial agent disposed on the exterior surface of the first and second expandable members proximate the compartment.

21. The adjustable balloon catheter according to claim 19, wherein the at least one beneficial agent release structure includes at least one reservoir defined by the exterior surface of the first and second expandable members proximate the compartment.

22. The adjustable balloon catheter according to claim 19, wherein the at least one beneficial agent release structure includes a pore structure defined in the exterior surface of at least one of the first and second expandable member, the pore structure in fluid communication with the compartment.

23. The adjustable balloon catheter according to claim 22, wherein the inner tubular member further has a fluid lumen defined therein, the fluid lumen extending from the proximal end portion to the distal end portion of the inner tubular member, the pore structure in fluid communication with the fluid lumen.

24. The adjustable balloon catheter according to claim 23, further comprising a source of beneficial agent in fluid communication with the fluid lumen to introduce beneficial agent through the fluid lumen and out the pore structure into the compartment when the first and second expandable members are in the inflated condition and the outer tubular member is retracted proximal to the compartment.

25. The adjustable balloon catheter according to claim 23, further comprising a vacuum source in fluid communication with the fluid lumen to draw negative pressure in the compartment when the first and second expandable members are in the inflated condition and the outer tubular member is retracted proximal to the at least one compartment.

26. The adjustable balloon catheter according to claim 22, wherein the pore structure includes a plurality of pores defined in the exterior surface of the first and second expandable members.

27. The adjustable balloon catheter according to claim 26, wherein the plurality of pores are arranged in a pattern along the first and second expandable members.

28. The adjustable balloon catheter according to claim 27, wherein the pattern is uniform along the working length of the first and second expandable members.

29. The adjustable balloon catheter according to claim 27, wherein the plurality of pores are substantially similar in size.

30. The adjustable balloon catheter according to claim 27, wherein the plurality of pores vary in size.

31. The adjustable balloon catheter according to claim 19, wherein the inner tubular member includes a radiopaque distal marker proximate the distal end portion.

32. The adjustable balloon catheter according to claim 31, wherein the inner tubular member further includes at least one proximal marker spaced proximally of the distal marker.

33. A method of delivering a beneficial agent, comprising:
providing an adjustable balloon catheter including:
an inner tubular member having a proximal end portion, a distal end portion, and a length therebetween, the inner tubular member further having an inflation lumen and a fluid lumen defined therein,
at least one expandable member coupled to the distal end portion of the inner tubular member and having an inner chamber defined therein in fluid communication with the inflation lumen, the at least one expandable member transitionable between a deflated configuration and an inflated configuration by inflation medium from the inflation lumen, wherein the at least one expandable member is in fluid communication with the inflation lumen, the at least one expandable member further having an exterior surface along a working length thereof, the exterior surface defining at least a portion of a compartment along the working length when in the inflated configuration, the exterior surface having at least one beneficial agent release structure defined therein, the at least one beneficial agent release structure including at least one pore structure in fluid communication with the fluid lumen and in fluid communication with the at least one compartment when in the inflated configuration,
an outer tubular member movable relative to the inner tubular member, the outer tubular member including a distal end, the outer tubular member being moveable between an extended position disposed over the at least one expandable member and a retracted position proximal to the extended position, the outer tubular member being selectively positioned between the extended position and the retracted position to define an exposed length of the working length of the expandable member; and
retracting the outer tubular member in a proximal direction proximal to the compartment to define the exposed length of the working length of the at least one expandable member;
inflating the exposed length of the at least one expandable member to the inflated configuration by inflation medium from the inflation lumen;
introducing beneficial agent through the fluid lumen and releasing beneficial agent from the pore structure into the compartment when the at least one expandable member is in the inflated condition and the outer tubular member is retracted proximal to the compartment; and
deflating the at least one expandable member to the deflated configuration.

34. A method of delivering a beneficial agent, comprising:
providing an adjustable balloon catheter including:
an inner tubular member having a proximal end portion, a distal end portion, and a length therebetween, the inner tubular member further having an inflation lumen and a fluid lumen defined therein;
a first expandable member and a second expandable member coupled to the distal end portion of the inner tubular member and each having an inner chamber defined therein in fluid communication with the inflation lumen wherein the second expandable member proximate the first expandable member, the first and second expandable members transitionable between a deflated configuration and an inflated configuration by inflation medium from the inflation lumen, the first and second expandable members in fluid communication with the inflation lumen, the first and second expandable members each further having an exterior surface along a working length thereof, the exterior surface of the first expandable member defining at least a portion of a compartment along the working length of the first expandable member when in the inflated configuration and the exterior surface of the second expandable member defining at least a second portion of the compartment along the working length of the second expandable member when in the inflated configuration,
at least one beneficial agent release structure associated with the compartment, the at least one beneficial agent release structure disposed between the first and second expandable members;
an outer tubular member movable relative to the inner tubular member, the outer tubular member including a distal end, the outer tubular member being moveable between an extended position disposed over the first and second expandable members and a retracted position proximal to the extended position, the outer tubular member being selectively positioned between the extended position and the retracted position to define an exposed length of the working length of the second expandable member;
retracting the outer tubular member in a proximal direction to define the exposed length of the working length of the at least one of the first and second expandable members and proximal to the compartment;
inflating the first and second expandable members to the inflated configuration by inflation medium from the inflation lumen;
releasing beneficial agent from the at least one beneficial agent release structure into the compartment; and
deflating the first and second expandable members to the deflated configuration.

35. The method according to claim 34, further comprising altering pressure within the compartment after the beneficial agent has been released therein.

* * * * *